United States Patent
Knoll et al.

(10) Patent No.: US 10,258,598 B2
(45) Date of Patent: Apr. 16, 2019

(54) COMPOUNDS FOR USE IN THE PREVENTION OR TREATMENT OF CANCER

(71) Applicants: SEMMELWEIS UNIVERSITY, Budapest (HU); FUJIMOTO CO. LTD., Osaka (JP); Eckhardt Sándorná, Budapest (HU)

(72) Inventors: József Knoll, Budapest (HU); Ildikó Miklya, Budapest (HU); Péter Ferdinandy, Budapest (HU); Dezso Schuler, Budapest (HU); Zsuzsanna Schaff, Budapest (HU); Sándor Eckhardt, Budapest (HU)

(73) Assignees: Semmelweis University, Budapest (HU); Fujimoto Co. Ltd., Osaka (JP)

( * ) Notice: Subject to any disclaimer, the term of this patent is extended or adjusted under 35 U.S.C. 154(b) by 0 days.

(21) Appl. No.: 15/533,067

(22) PCT Filed: Dec. 7, 2015

(86) PCT No.: PCT/IB2015/059405
§ 371 (c)(1),
(2) Date: Jun. 5, 2017

(87) PCT Pub. No.: WO2016/088111
PCT Pub. Date: Jun. 9, 2016

(65) Prior Publication Data
US 2017/0340582 A1 Nov. 30, 2017

(30) Foreign Application Priority Data

Dec. 5, 2014 (EP) .................................. 14196623

(51) Int. Cl.
*A61K 31/137* (2006.01)
*A61P 35/00* (2006.01)
*C07C 211/27* (2006.01)
*A61K 31/343* (2006.01)

(52) U.S. Cl.
CPC .......... *A61K 31/343* (2013.01); *A61K 31/137* (2013.01); *A61P 35/00* (2018.01); *C07C 211/27* (2013.01)

(58) Field of Classification Search
CPC ...... A61K 31/137; C07C 211/27; A61P 35/00

USPC .................................. 564/381, 382; 514/654
See application file for complete search history.

(56) References Cited

U.S. PATENT DOCUMENTS

| 5,783,606 A * | 7/1998 | Tatton .................. A61K 31/137 514/649 |
| 6,214,859 B1 | 4/2001 | Yoneda et al. |
| 6,391,914 B1 | 5/2002 | Knoll et al. |

FOREIGN PATENT DOCUMENTS

WO  88/ 02254 A1  4/1988

OTHER PUBLICATIONS

Miklya I. Molecular Psychiatry (2016) 21, 1499-1503.*
Pccompound-1-47,Create Date Mar. 25, 2005 to Create Date Feb. 13, 2015.*
Thyagarajan et al.: "Antitumor effect of L-deprenyl in rats with carcinogen-induced mammary tumors", Cancer Letters, 1998, vol. 123(2), pp. 177-183.
Kitani et al.: "Assessing the effects of deprenyl on longevity and antioxidant defenses in different animal models", Annals of the New York Academy of Sciences, 1998, vol. 854, pp. 291-306.
Kitani et al.: "The necessity of having a proper dose of (-)deprenyl (D) to prolong the life spans of rats explains discrepancies among different studies in the past", Annals of the New York Academy of Sciences, 2006, vol. 1067(1), pp. 375-382.
Knoll: "How selegiline ((-)-deprenyl) slows brain aging", Bentham Science Publishers, 2012.
Farer: "Deprenyl: 50 years of life enhancement and life extension", Aging Matters Magazine, 2014, issue 5, pp. 8-11.

* cited by examiner

*Primary Examiner* — Venkataraman Balasubramanian
(74) *Attorney, Agent, or Firm* — Jason D. Voight

(57) ABSTRACT

The invention relates to the field of prevention and treatment of cancer, in particular suppression of tumor manifestation. The invention also relates to compounds for use in this field. A novel tumor manifestation suppression (TMS) regulation in a mammalian brain is recognized. The invention relates to compounds, pharmaceutical preparations, in particular medicaments for use in the prevention and treatment of cancer, in particular suppression of tumor manifestation based on said TMS regulation as well as methods for the same.

16 Claims, 7 Drawing Sheets

Kaplan-Meier test P=0.0054 (**P<0.01)

Kaplan-Meier test P=0.1155 (ns)

US 10,258,598 B2

COMPOUNDS FOR USE IN THE PREVENTION OR TREATMENT OF CANCER

This is the national stage of International Application PCT/IB2015/059405, filed Dec. 7, 2015.

TECHNICAL FIELD OF THE INVENTION

The invention relates to the field of prevention and treatment of cancer, in particular suppression of tumor manifestation. The invention also relates to compounds for use in this field. The invention also relates to pharmaceutical preparations, in particular medicaments for use in the prevention and treatment of cancer, in particular suppression of tumor manifestation as well as methods for the same.

BACKGROUND ART

The mechanism of tumor suppression is an area of intensive research today. Significant efforts are made to utilize tumor suppressor genes, or antioncogenes that may protect a cell from one step on the path to cancer. The loss of these genes may be even more important than proto-oncogene or oncogenes activation for the formation of many kinds of human cancer cells (Weinberg, Robert A 2014). A variety of therapies are attempted. For example immunotherapy, stimulating or helping the immune system to fight cancer, have come into view since 1997, and this continues to be an area of active research (Waldman T. A. 2003). However, the outcome of treatments aiming at suppression of tumor manifestation are highly uncertain. It has been recognized for a long time that certain compounds enhance catecholaminergic or serotonergic activity in the brain which may be unrelated to MAO-B inhibition (Knoll and Miklya, 1994).

This enhancer regulation involves the existence of enhancer—sensitive neurons in the brain capable of working in a split-second on a significantly higher activity level. It has been found that an endogenous enhancer substance Phenylethylamine (PEA) enhances the impulse—propagation mediated release of monoaminergic substances, including the catecholamines dopamine and noradrenalaine, and serotonin [see Knoll J (2001) CNS Drug Rev 7:317-345 and Knoll J (2003) Neurochem Res 28:1187-1209]. Enhancer substances may have their own receptors on specific enhancer-sensitive neurons that facilitate the release of neurotransmitters depending on neuronal firing activity.

The enhancer regulation also plays an important role in development of acquired drives, that are important determinants of our lifelong activity and equilibrium. Enhancer regulation of these cortical neurons is required for manifesting acquired drives and reaching our goals. Enhancer regulation affects our learning capacity and regulates our perception through sensory neurons. The optimal activity of these cortical and brainstem neurons relies upon on their endogenous enhancer substances to keep them active and balanced. Having proper and active enhancer activity as we age is essential to a long, fulfilling, active and healthy lifespan [see Knoll J (2003) Neurochem Res 28:1187-1209].

The enhancer compounds are a kind of "neuroamplifiers". They enhance the electronic coupling in the synaptic gap junction of linked regions of cells for greater signal strength in the pulses of neurotransmitter release. This effect is related to the increasing the signal-to-noise ratio for stronger signal firing. Thus, by this mechanism the release of monoamine neurotransmitters is more efficiently coupled to the electrical impulse that triggers their release, and the activity of monoaminergic neurons is upregulated resulting in an immediate and strong activity. These finding have been heralded as being of great importance for cognitive enhancement or clinical importance in Parkinson's disease and Alzheimer's disease, where the nigrostriatal tract and mesolimbic-cortical circuits under-function and for effectively treating depression due to an under-activity of both dopamine and noradrenalin neurons [EP1052259B1 corr. to WO 2000/026204, EP 0 957 080 B1 corr. to WO 1999/007667, Knoll J (2001) CNS Drug Rev 7:317-345, Miklya I (2011) InTech Open Acces Publisher (www.intechopen-.com), pp. 77-100.]. This catecholaminergic and serotonergic system keep the higher brain centers active and the continuous decline of the mesencephalic enhancer regulation during the post-developmental phase of life is somehow related with age [Knoll J (1994) Pharmacol Toxicol 75:65-72].

A number of compounds which potentially have an enhancer activity have been synthesized and proposed for the treatment of various neurological type disorders.

For example, many ethylamine derivatives have already been disclosed. Certain 6-(2-aminoethyl)-benzoxazolinone derivatives are described as anti-anxiety drugs and drugs for heart failure in EP 110,781. Moreover, aminoalkylbenzoxazinone derivatives are described as useful remedies for damage of central nervous system in FR 2,035,749. Moreover, the psychotropic alkylamines are taught for use in medicaments in JP 06-99,420 (examined publication). Typically these compounds, while are capable of releasing catecholamines from their depos in the central nervous system, in fact easily deliberate an excess amount of catecholamines resulting in side effects as neurotoxicity, just as stimulants.

One of the most prominent compound in this circle is (−)-Deprenyl (Selegiline, Eldepryl, Jumex, Emsam, Zelepar), originally introduced as the first selective inhibitor of B-type monoamino oxidase (MAO). Deprenyl is registered to treat Parkinson's disease, Alzheimer's disease, major depression disease, and is widely used as an anti-aging compound. The group of the present inventor demonstrated previously that (−)-deprenyl in lower doses, devoid of MAO-B inhibitory potency act as a highly specific catecholaminergic activity enhancer substance. It enhances the impulse propagation generated release of the transmitter. It has been demonstrated in earlier longevity studies performed with (−)-deprenyl that due to its enhancer effect rats maintained on lifelong (−)-deprenyl, preserved their learning ability and sexual activity significantly longer, and lived significantly longer than their placebo-treated peers (Knoll and Miklya, 1995).

The age-related decay in the supply of the brain with PEA, due to the progressive increase of MAO-B activity in the aging brain, and dopamine, due to the better than average decline of the dopaminergic neuronal activity during the post-developmental phase of life, are irresistible biochemical lesions of aging. Previous findings that Deprenyl (FIG. 1) prolongs life were confirmed in rats, mice, hamsters, and dogs (Table 1).

TABLE 1

Previous longevity studies and the confirmation
of the finding (m—male; f—female)

| Year | Species | Confirmation | Species |
|---|---|---|---|
| 1988 | Knoll | Wistar Logan Rats (m) | |

TABLE 1-continued

Previous longevity studies and the confirmation
of the finding (m—male; f—female)

| Year | Species | | Confirmation | Species |
|---|---|---|---|---|
| 1989 | Knoll, Dalló, Yen | Wistar Logan Rats (m) | | |
| 1990 | | | Milgram et al. | Fischer 344 Rats (m) |
| 1993 | | | Kitani et al. | F 344 Rats (m) |
| 1994 | Knoll, Yen, Miklya | Wistar Logan Rats (m) | Freisleben et al. | Mice (m) |
| 1996 | Dalló, Köles | Wistar Logan Rats (f) | Archer et al. | Mice (m, f) |
| 1997 | | | Bickford et al. | F344 rats (m) |
| | | | Ruehl et al | Beagle dogs |
| | | | Stoll et al. | Syrian hamsters (f) |

It has been shown that from weaning until sexual maturity an increased enhancer regulation operates in the catecholaminergic and serotonergic neurons. This mechanism terminates developmental longevity and constitutes the foundation of the transition from adolescence to adulthood (Knoll et al., 2000).

The enhancer-sensitive catecholaminergic and serotonergic neurons work before weaning at a low, "economic" level, which is dramatically intensified after weaning. The tense excitement remains unchanged during the developmental phase of life, from weaning until sexual maturity. Sexual hormones (estrone, testosterone) return the enhanced catecholaminergic and serotonergic activity to the pre-weaning, "economy" level, terminating the developmental phase of life. This change is also the beginning of the slow, continuous decay of the enhancer regulation (aging) until "natural death". It is obvious that only the development of a safe and efficient preventive pharmacological intervention, starting immediately after the completion of sexual maturity, can significantly slow brain aging. In the extremely low dose range in which they exert their specific enhancer effect, the enhancer substances selectively transform the lower performing enhancer sensitive neurons into better performing ones.

In retrospection the outcome of the second longevity study, published in 1994, was the first undeniable proof of this mechanism. In a longevity study out of 1600, 28-week-old males of the robust, long-living Wistar-Logan strain of rats, the 94 sexually lowest performing (LP) and 99 sexually highest performing (HP) ones were selected and treated with saline and Deprenyl, respectively, for life. The saline treated LP rats (n=44) lived 134.58±2.29 weeks, and their HP-peers lived 151.24±1.36 weeks (P<0.001). The Deprenyl treated LP rats (n=49) lived significantly longer than their saline treated peers and lived as long as the saline-treated HP rats. Deprenyl treatment also transformed the innate HP rats (n=50) into better performing ones. They lived 185.30±1.96 weeks. Out of the 50 rats, 17 lived longer than the maximum lifespan ever observed during a long observation period on hundreds of untreated or saline treated rats in the strain used in our studies.

The enhancer effect has a bi-modal, double bell-shaped concentration-effect curve wherein one of the effective concentration ranges of the enhancer substance is needed for a good performance. The lower curve is related to the specific enhancer effect whereas the one at higher concentrations to the non-specific effect.

(R)-1-(benzofuran-2-yl)-2-propylamino pentane ((−)-BPAP or BPAP in short) is a later developed enhancer substance, for the time being known as the most potent and selective one. The development of BPAP exerts its specific enhancer activity even in femto/picomolar concentration (Knoll et al., 1999). Experimental and clinical studies with Deprenyl and BPAP proved that preventive administration of synthetic enhancer substances during post-developmental life significantly slows the aging-related decay of behavioral performances and prolongs life. In humans, maintenance from sexual maturity on Deprenyl is today the only available treatment with a promising chance to reach this aim and afford chance to prevent or delay the onset of aging-related neurodegenerative diseases, such as Parkinson's disease and Alzheimer's disease.

Considerable attention has been paid to the activity enhancer effect of monoaminergic neurons, preferably catecholaminergic enhancer effect (CAE) effect of catecholaminergic neurons, which is an action to enhance the catecholamine release due to amplification of the membrane potential dependent exocytosis, and which is different from the above releasing action by displacing catecholamine from their storage [Life Sci., 58, 945-952 (1996), WO1999/007667 and WO2000/026204]. Compounds enhancing catecholamine release by CAE effect were found useful in psychotropic compositions, antidepressants, compositions for the treatment of Parkinson's disease and/or of Alzheimer's disease (WO 1999/007667, also published as EP957080). In WO2000026204 the respective optical isomers from organic amine compounds in WO1999007667 by means of the optical resolution is described. These optically active isomers were found useful remedies by pharmacological screening for the same group of disease, in particular for treating Parkinson's disease, and/or Alzheimer's disease.

Deprenyl is preferentially a CAE substance and a very weak enhancer of the serotonergic neurons.

Kitani K et al. (Kitani K et al., 1998) have proposed, based on animal models that Deprenyl provides an antioxidant effect in animals and thereby it may prevent tumor development in animal. However, the authors are silent about any low dose tumor manifestation suppressor effect due to a specific cathecholaminergic enhancer effect.

While in ThyagaRajan, S. et al (ThyagaRajan, S. et al. 1998) have found that Deprenyl, as a MAO-B inhibitor, would inhibit the development of mammary tumors by exerting a neuroprotective effect on the tuberoinfundibular dopaminergic (TIDA) neurons in the medial basal hypothalamus (MBH) at a 0.25 mg/kg body weight or higher, they have not recognized that a tumor suppressor effect is possible in a much lower dose exerting a specific enhancer effect, e.g. in a dose as low as or lower than 0.01 mg per kg body weight.

To the best of the present inventors' knowledge, it has never been suggested in the art that the catecholaminergic system would have been linked to any mechanism in the brain effecting tumour manifestation.

Problem to be Solved by the Invention

There is still a need in the art to provide suppression of manifestation of tumors by a long term and low dose administration of a safe compound.

Means to Solve the Problem

It has been unexpectedly discovered by the present inventors that neuronal activity enhancer compounds having a specific CAE effect have also a suppressive effect of tumor manifestation. Thus, the present inventors have made serious efforts to elaborate the present invention.

BRIEF DESCRIPTION OF THE INVENTION

The present invention relates to a compound or a pharmaceutically acceptable salt thereof, wherein said compound is a neuronal activity enhancer compound which is a monoaminergic activity enhancer compound which enhances impulse propagation mediated release of a monoamine neurotransmitter from monoaminergic neurons in the central nervous system, for use in preventing or treating a cancer or a metastasis thereof.

Preferably, said compound is administered or is for administration in specific enhancer dose.

Preferably the effect of the monoaminergic activity enhancer compound, i.e. the enhancement of impulse propagation mediated release of a monoamine neurotransmitter from monoaminergic neurons is measurable or detectable or measured or detected, either directly or indirectly among others by the following methods:

- by measuring the amount of a cathecholamine, preferably [3H]-norepinephrine, [3H]-dopamine released to electrical stimulation from an isolated rat brain stem in the presence of said enhancer compound;
- by a conditioned avoidance reflex (CAR) assay e.g. with murines having learning deficit e.g. due to tetrabenazine-treatment, which can be antagonized by the administration of a synthetic cathecholaminergic activity enhancer (CAE) substance, whereas selective inhibition of B-type MAO or inhibition of the reuptake of catecholamines or serotonin, respectively is ineffective; and
- by administration of a candidate enhancer compound in very broad dose range, wherein a bi-modal, bell-shaped concentration effect curve is characteristic to the enhancer effect (at least the lower range being below that of the MAO inhibition, if any); wherein the lower range shows the "specific enhancer effect" whereas the higher range the "non-specific enhancer effect" (Knoll J 2012).

In particular, the present invention relates to a compound according to general formula I or a pharmaceutically acceptable salt thereof, wherein said compound is a monoaminergic activity enhancer compound which enhances impulse propagation mediated release of a monoamine neurotransmitter from monoaminergic neurons in the central nervous system, for use in preventing or treating a cancer or a metastasis thereof,

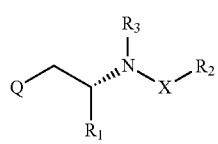

wherein in general formula I,

Q is a substituted or unsubstituted 6 to 10 membered cyclic or heterocyclic group comprising one 6 membered cyclic or heterocyclic ring having a delocalized pi electron system, wherein if Q is substituted, said substituent being selected from the group consisting of hydrogen, hydroxyl, C1-4 alkyl, C1-4 alkoxy and halogen, wherein Q, if comprises one heterocyclic ring said ring preferably comprises at most one to three, preferably one to two heteroatoms, wherein said heteroatoms are preferably selected from O, N and S, X is a methylene, i.e. >CH2, or an ethylene, i.e >CH—CH2, >NH, >NCH3- or —O—

R1 is hydrogen, C1-6 alkyl, C2-4 alkenyl, C2-4 alkynyl or C2-4 alkylcarbonyl,

R2 is hydrogen, C1-4 alkyl, C2-4 alkenyl, C2-4 alkynyl, C2-4 alkylcarbonyl, C6-10 aryl or C7-11 arylalkyl;

R3 is hydrogen, methyl or ethyl, wherein any one of R1, R2 and R3, if different from hydrogen, independently from each other is either unsubstituted or substituted, wherein if substituted said substituent preferably being selected from the group consisting of hydrogen, hydroxyl, C1-4 alkyl, C1-4 alkoxy and halogen, with the proviso that if the substituent is C1-4 alkyl or C1-4 alkoxy the substituent is shorter, i.e. has less carbon atoms, than R1, R2 or R3 which is substituted therewith.

Preferably Q is substituted with one or two substituent(s) or is unsubstituted.

Preferably any one of R1, R2 and R3 is substituted with one or two substituent(s) or is unsubstituted.

Preferably Q is a C6 cyclic or heterocyclic group having a delocalized pi electron system.

The delocalized pi electron system may or may not extend to the whole ring(s). Preferably the pi electron system is aromatic and thus preferably Q is aromatic group.

The compound according to general formula I is either an S or an R configuration compound at said chirality center or stereocenter, preferably an R configuration compound according to the Cahn-Ingold-Prelog and the compound has the formula I:

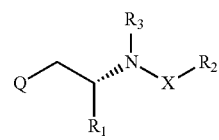

wherein Q, X, R1, R2 and R3 are as defined above or herein.

Said compound is for use in preventing or treating a cancer or a metastasis in a specific enhancer dose.

In a preferred embodiment in the compound of formula I X is a methylene group i.e. is CH2.

In a further preferred embodiment X is a methylene group i.e. is CH2 and the compound is an R configuration compound and the compound has the general formula II

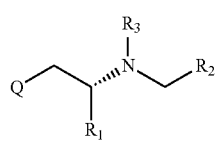

The monoaminergic activity enhancer compound is a catecholaminergic activity enhancer (CAE) substance and the monoaminergic neurons are catecholaminergic neurons. Preferably said compound is administered in specific enhancer dose.

In a further preferred embodiment the invention relates to a monoaminergic activity enhancer compound according to general formula II or a pharmaceutically acceptable salt thereof for use in the prevention or inhibition of a cancer or a metastasis thereof, wherein in formula II Q is a group consisting of is a substituted or unsubstituted unsaturated, preferably aromatic, six-membered ring which may or may not have one or two heteroatoms, wherein if Q is substituted, said substituent is selected from the group consisting of hydrogen, hydroxyl, C1-4 alkyl, C1-4 alkoxy and halogen, preferably Q is substituted with one or two substituent(s) or is unsubstituted, $R_1$ is a $C_{1-5}$ alkyl, preferably is methyl or ethyl or propyl;

$R_2$ is $C_{1-4}$ alkyl, $C_{2-4}$ alkenyl or $C_{2-4}$ alkyne; preferably $C_{2-3}$ alkenyl or $C_{2-3}$ alkyne;

$R_3$ is hydrogen, methyl or ethyl.

In a preferred embodiment Q is an unsubstituted aromatic, six-membered ring.

Alternatively, the present invention relates to a monoaminergic activity enhancer compound according to general formula II or a pharmaceutically acceptable salt thereof for use in the prevention or inhibition of a cancer or a metastasis thereof, preferably in an amount which stimulates enhancer-sensitive neurons in the brain and having a specific enhancer effect thereon, wherein in formula II Q is a substituted or unsubstituted phenyl group, wherein if said phenyl is substituted, said substituent being selected from the group consisting of hydrogen, hydroxyl, $C_{1-4}$ alkyl, $C_{1-4}$ alkoxy and halogen, preferably said phenyl being unsubstituted, $R_1$ is a $C_{1-5}$ alkyl, preferably is methyl or ethyl or propyl;

$R_2$ is $C_{1-4}$ alkyl, $C_{2-4}$ alkenyl or $C_{2-4}$ alkynyl; preferably $C_{2-3}$ alkenyl or $C_{2-3}$ alkynyl;

$R_3$ is hydrogen, methyl or ethyl, preferably hydrogen or methyl.

Alternatively, the present invention relates to a monoaminergic activity enhancer compound according to general formula II or a pharmaceutically acceptable salt thereof for use in the prevention or inhibition of a cancer or a metastasis thereof, wherein in formula II Q is a substituted or unsubstituted phenyl group, wherein if said phenyl is substituted, said substituent being selected from the group consisting of hydrogen, hydroxyl, $C_{1-4}$ alkyl, $C_{1-4}$ alkoxy and halogen, preferably said phenyl being substituted with one or two substituent(s) or being unsubstituted, $R_1$ is methyl, ethyl or propyl;

$R_2$ is $C_{2-4}$ alkenyl, $C_{2-4}$ alkynyl or $C_{2-4}$ alkylcarbonyl;

$R_3$ is hydrogen, methyl or ethyl.

The pharmaceutically acceptable salt can be an acid addition salt.

In an embodiment the six-membered ring comprises one or two heteroatom(s) in Q wherein preferably the one or two heteroatom(s) in Q is(are) selected from O and N.

Preferably, in the compound for use according to the invention $R_2$ is selected from $C_{2-3}$ alkenyl and $C_{2-3}$ alkynyl.

Preferably, Q is a phenyl group.

Preferably, Q is a phenyl group and $R_1$ is selected from methyl and ethyl and $R_2$ is selected from $C_{2-3}$ alkenyl and $C_{2-3}$ alkyne.

In a preferred embodiment Q is a phenyl and $R_1$ is methyl, ethyl, propyl or butyl, preferably methyl, ethyl or propyl;

$R_2$ is $C_{1-4}$ alkyl, $C_{2-4}$ alkenyl or $C_{2-4}$ alkynyl;

$R_3$ is hydrogen, methyl or ethyl.

In a preferred embodiment the compound according to the invention has general formula IV

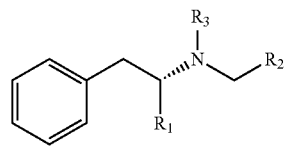

IV wherein in general formula IV $R_1$, $R_2$ and $R_3$ are as defined for embodiments wherein Q is a group consisting of is a substituted or unsubstituted unsaturated, preferably aromatic, six-membered ring which may or may not have one or two heteroatoms or preferred embodiments thereof.

In a preferred embodiment Q is a phenyl and $R_1$ is ethyl or propyl;

$R_2$ is methyl, ethyl or propyl, preferably ethyl;

$R_3$ is hydrogen, methyl or ethyl, preferably hydrogen or methyl, more preferably hydrogen.

In a highly preferred embodiment the monoaminergic activity enhancer compound is (R)-1-Phenyl-N-propylpentan-2-amin [(−)-PPAP].

In a preferred embodiment Q is a phenyl and $R_1$ is methyl or ethyl and $R_2$ is $C_{2-3}$ alkenyl or $C_{2-3}$ alkyne. Preferably $R_3$ is hydrogen, methyl or ethyl.

In a preferred embodiment $R_2$ is ethynyl.

In a highly preferred embodiment the monoaminergic activity enhancer compound is (R)—N-methyl-N-(1-phenylpropan-2-yl)prop-2-yn-1-amine (Selegiline or (−)-Deprenyl).

Preferably the compound is used in an amount which stimulates enhancer-sensitive neurons or in an amount which enhances catecholamine release in the brain or in the central nervous system.

Preferably the compound is used in an amount which enhances catecholamine release in the brain or in the central nervous system.

Preferably, said compound is administered in a daily dose lower than 0.01 mg per kg body weight, preferably lower than 0.005, 0.0025 mg/kg body weight. Preferably, the compound is administered in a daily dose lower than 0.0025 mg/kg body weight. Preferably this is a specific enhancer dose.

Preventing or treating a cancer or metastasis thereof is preferably accompanied by the suppression of the manifestation thereof; in this case it is understood as suppressing the manifestation of said cancer or metastasis.

In an embodiment the cancer is a malignant tumor or neoplasm selected from the group consisting of carcinomas, sarcomas, leukemias, lymphomas and germinomas.

In a preferred embodiment the malignant tumor is a carcinoma or a sarcoma, preferably a carcinoma or a sarcoma of the connective tissue.

In a highly preferred embodiment the malignant tumor is selected from the group consisting of fibromyxosarcoma, adenocarcinoma, colon carcinoma and liver metastasis.

In an embodiment the subject is a warm-blooded animal, preferably a mammal, preferably a human.

Preferably the compound is administered in a low dose wherein the specific enhancer effect is exerted.

Preferably the compound is administered in a low dose wherein no other effect but the enhancer effect thereof is known or can be shown or exerted (specific enhancer effect).

Preferably, said compound is administered to the subjects for a long period, preferably for at least 1, 2, 3, 5, 6, 8 or 10 months or for at least 1, 2, 3, 4, 5 or 6 years, or for a time-period longer than 1%, 2% or preferably 5% of the expectable life-time of the subject.

Preferably, the subject is a human adult and the time-period of administration is longer than 1 year, 2 years or preferably 5 years.

In a preferred embodiment the subject is a sexually mature subject, preferably an adult subject.

In a preferred embodiment the subject shows no manifestation of cancer, e.g. a malignant tumor or neoplasm. Preferably the compound is used for prevention or prophylaxis of a cancer or a metastasis thereof.

The invention also relates to a pharmaceutical composition or a medicament comprising the compound for use according to the invention as an active compound in an amount in which said compound enhances catecholamine release in central nervous system.

Preferably, the medicament comprises the compound for use of the invention, as defined above or herein or hereinbelow as an active compound, wherein the optical purity of the compound is higher than 70%, preferably higher than 80% or 90% or 95% or 97% or 98% or 99%.

The invention also relates to method for preventing or treating a cancer or metastasis thereof or treating a subject to suppress manifestation of a cancer or metastasis in said subject, comprising administering to said subject a compound as defined above or herein in a therapeutic amount.

Definitions

A "pharmaceutical composition" of the invention is a composition of matter which comprises at least one biologically active substance suitable for the treatment of cancer as defined herein. Pharmaceutical compositions may also comprise further biologically active substances useful e.g. in a combination therapy, for example a chemotherapeutic compound which may be a cytotoxic agent. Furthermore, the compositions may comprise an adjunctive compound to prevent or reduce the incidence of nausea and vomiting associated with chemotherapy. Adjunctive agents are well known in the art. Furthermore, the compositions may include immunotherapeutic agents.

A "medicament" is a pharmaceutical composition the effectiveness in animals, e.g. in warm-blooded animals or in mammals or in humans is supported by evidence, preferably which is registered at a health authorization or health agency of a country or a region or a community of countries.

"Therapeutic amount" of a compound refers to an amount of the compound effective in treating, combating, ameliorating, preventing or improving a cancer condition, in particular a cancer or metastasis thereof as disclosed herein. Preferably, the therapeutic amount of a compound of the invention is lower, preferably significantly lower than the amount in which it exerts an other therapeutic effect, e.g. MAO inhibition, e.g. MAO-B inhibition.

A "cancer" is understood herein as a condition of a subject characterized by malignant unregulated or uncontrolled proliferation of cancer cells of said subject. The proliferation usually result in or develop a lump or a mass of cells which is called a "neoplasm" or "tumor" which are included in the term cancer.

A cancer is considered herein as "malignant" if it has a tendency to result in a progressive worsening of the condition of the subject, i.e. has a deleterious effect in the subject and to potentially result in his/her/its death.

In an embodiment cancer is or may also considered as malignant if the lump or mass of cells (e.g. a neoplasm or tumor) develop initially appears or diagnoses as not to be malignant, i.e. "benign" but (i) carry the risk of becoming malignant, or (ii) becomes malignant later in time.

"Manifestation" of cancer is understood herein as the appearance of a detectable or measurable sign or indication or specific evidence that the cancer is present, preferably the cancer is manifested when at least one symptom thereof is present. "Manifestation" of cancer can be quantitatively characterized or thereby the level of manifestation is assessed.

"Suppression" of manifestation of cancer is a result of a therapy (or therapeutic intervention) or treatment wherein manifestation of cancer does not occur, or occurs less frequently e.g. in a lesser number of cases or with a smaller probability, or is prevented or reduced; or the level of manifestation is lower as compared with an appropriate control or control treatment. A control can be a setting or treatment wherein the therapy or the treatment is not applied or a placebo is administered, e.g. in the same subject or a control subject or a control group of subjects; or the control can be a control value.

"Metastasis" is the process wherein cancer cells from the cancer spread from their original site to other parts of the body through the lymphatic system or blood stream whereas this process results in a "metastasis" or multiple "metastases".

An "animal" refers to vertebrates, preferably warm-blooded animals, preferably mammals. In a broader sense the term animal and preferably mammal included human being. Optionally, in a narrower sense the term animal does not include a human being. Said animal may be selected from fishes, reptiles, amphibians, birds or mammals. Preferably the animal is a mammal.

A "subject" is understood herein as an animal or a human being to whom treatment, including prophylactic treatment, with the preparations or compositions of the present invention, is or is to be provided. Preferably the subject is a warm-blooded animal, a mammal or a human. Preferably the subject is a patient.

A "patient" is a subject who is under medical diagnosis, observation or treatment. Preferably the patient is a subject having a cancer. Preferably the treatment is preventive or curative.

An "enhancer compound" is a neuronal activity enhancer compound (preferably a monoaminergic activity enhancer compound, in particular or more preferably a "catecholaminergic enhancer compound", CAE compound or "serotonergic enhancer compound", SAE compound) is capable of exciting in a dose-dependent manner at least a subset of enhancer sensitive neurons, preferably monoaminergic neurotransmitter releasing (preferably catecholaminergic and serotonergic) neurons, respectively, without inhibiting monoamine-oxidase-A (MAO-A), preferably without inhibiting MAO-B. In particular, a dose range can be defined wherein said compound enhances impulse propagation mediated release of a monoamine neurotransmitter from monoaminergic neurons in the central nervous system. Preferably due to the enhancing effect on the monoaminergic neurotransmitter, preferably a catecholamine or serotonine, release occurs through amplification of the membrane potential dependent exocytosis. Preferably an enhancer compound increases the excitability of enhancer-sensitive neurons.

Preferably, an enhancer compound enhances catecholamine release in the brain or in the central nervous system (CAE compound).

This cathecholaminergic enhancer effect (CAE effect) is measurable or detectable among others by the following methods:

by measuring the amount of [3H]-norepinephrine, [3H]-dopamine released to electrical stimulation from an isolated mammalian brain, preferably brain stem, preferably rat brain stem;

by a conditioned avoidance reflex (CAR) assay e.g. with murines having learning deficit e.g. due to tetrabenazine-treatment, which can be antagonized by the administration of a synthetic CAE substance or an A-type MAO inhibitor, whereas selective inhibition of B-type MAO or inhibition of the reuptake of catecholamines or serotonine, respectively is ineffective; and by administration of a candidate cathecholaminergic enhancer compound in very broad dose range, wherein a bi-modal, bell-shaped concentration effect curve is characteristic to the enhancer effect; wherein the lower range shows the "specific enhancer effect" whereas the higher range the "non-specific enhancer effect" (both ranges or at least the lower range being below that of the typical MAO inhibition dose).

In assessing or detecting the enhancer effect one or more of the above methods and optionally one or more further method(s) can be applied.

The term "comprise(s)" or "comprising" or "including" are to be construed herein as having a non-exhaustive meaning and allow the addition or involvement of further features or method steps or components to anything which comprises the listed features or method steps or components.

The expression "consisting essentially of" or "comprising substantially" is to be understood as consisting of mandatory features or method steps or components listed in a list, e.g. in a claim, whereas allowing to contain additionally other features or method steps or components which do not materially affect the essential characteristics of the use, method, composition or other subject matter. It is to be understood that "comprise(s)" or "comprising" or "including" can be replaced herein by (i.e. limited herein to) "consisting essentially of" or "comprising substantially" or if so required without addition of new matter.

It is to be understood that "comprise(s)" or "comprising" or "including" also can be limited to "consisting of" if so required.

"One or more" means one or more than one, preferably one, two or three, or one or two.

"Lower" alkyl, alkoxy etc. means preferably $C_{1-6}$, $C_{1-4}$, $C_{1-3}$ or $C_{1-2}$ alkyl or -alkoxy etc.

As used herein, the term "alkyl" alone or in combinations means a straight or branched-chain hydrocarbon group containing preferably from 1 to 6, preferably 1 to 4 or 1 to 3 carbon atom(s) or 1 to 2 carbon atom(s) (i.e. "$C_{1-6}$" "$C_{1-4}$" or "$C_{1-3}$" or "$C_{1-2}$" alkyl groups), such as methyl, ethyl, propyl, isopropyl, butyl, sec-butyl and t-butyl.

As used herein, the term "alkoxy" means an alkyl-O— group in which the alkyl group is as previously described. Non-limiting examples of suitable alkoxy groups include methoxy, ethoxy, n-propoxy, isopropoxy and n-butoxy, preferably methoxy. The bond to the parent moiety is through the ether oxygen.

As used herein, the term "aryl" refers to a mono- or bicyclic aromatic ring, optionally heterocyclic, e.g.

phenyl, pyridinyl, pyranyl, diazinyl, oxazinyl or dioxinyl, naphtyl, preferably 1-naphtyl or 2-naphtyl, indolyl, preferably 1-indol-2-yl or 1-indol-yl, bezodiazolyl, particularly 1,3-benzodiazolyl, preferably 1,3-benzodiazol-2-yl, benzofuranyl, particularly 1-benzofuranyl, preferably 1-benzofuran-2-yl or 1-benzofuran-3-yl; or benzodioxolyl, particularly 1,3-benzodioxolyl, preferably 1,3-benzodioxol-2-yl.

A "heterocyclic" compound or group or ring structure as used herein is a cyclic compound that has, besides carbon atom(s), atoms of at least one non-carbon element(s) as member(s) of its ring(s). Preferably the ring(s) of the heterocyclic compound is/are 5 to 6 membered ring(s).

An "alkenyl" as used herein, alone or in combinations, means a straight or branched-chain unsaturated hydrocarbon group containing at least one carbon-carbon double bond, said hydrocarbon group containing preferably from 2 to 6, preferably 2 to 4 or 2 to 3 or 2 carbon atom(s) (i.e. "$C_{2-6}$" "$C_{2-4}$" or "$C_{2-3}$" or "$C_{2-2}$" alkyl groups).

An "alkynyl" as used herein, alone or in combinations, means a straight or branched-chain unsaturated hydrocarbon group containing at least one carbon-carbon triple bond, said hydrocarbon group containing preferably from 2 to 6, preferably 2 to 4 or 2 to 3 or 2 carbon atom(s) (i.e. "$C_{2-6}$" "$C_{2-4}$" or "$C_{2-3}$" or "$C_{2-2}$" alkyl groups).

An "alkylcarbonyl" as used herein means an alkyl-CO— group comprising an alkyl and a carbonyl group composed of a carbon atom double-bonded to an oxygen atom, in which the alkyl group is as previously described. The bond to the parent moiety is through the carbon atom of the carbonyl group. ether oxygen.

An "arylalkyl" as used herein refers to an aryl alkyl group which is linked to the parent molecule through the alkyl group, which may be further optionally substituted with on or more, preferably one to three or one to two substituents as set forth above.

In a "saturated" group, ring or compound the chain of carbon atoms is linked together by single bonds only. An "unsaturated" group, ring or compound contains carbon-carbon double bonds or triple bonds or a delocalized, e.g. aromatic, pi electron system, such as those found in alkenes or alkynes or aryls, respectively.

As used herein, the term "fused ring" means that the ring is fused with a group to form a bicyclic group of the formula wherein a single bond between two member atoms of the rings is, together with said two members, common in, i.e. shared by the two rings.

An "alkyl substituent" is not larger, preferably smaller, i.e. shorter, i.e. consists of not more, preferably less chain atoms, preferably carbon atoms, than the group, moiety, e.g. Q, R1, R2 or R3 which is/are substituted thereby.

DETAILED DESCRIPTION OF THE INVENTION

Figure 1:
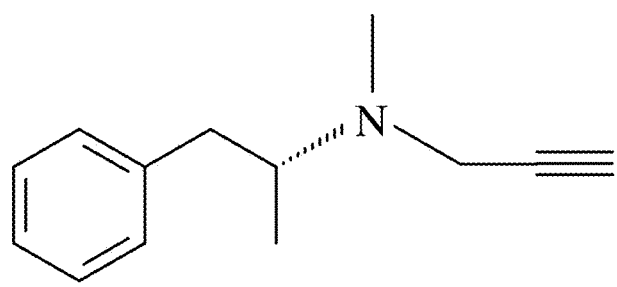
FIG. 1. The chemical structure of selegiline/(−)-deprenyl; Systematic (IUPAC) name: (R)—N-methyl-N-(1-phenyl-propan-2-yl)prop-2-yn-1-amine.
Figure 2:
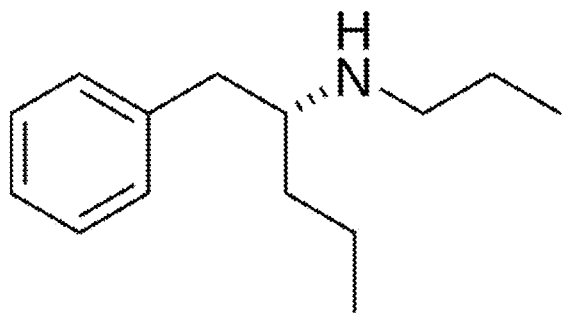
FIG. 2. The chemical structure of (−)-PPAP ((−)-1-Phenyl-2-propylaminopentane Systematic (IUPAC) name: (R)-1-Phenyl-N-propylpentan-2-amin.

It is easy to demonstrate that enhancer substances increase the excitability of enhancer-sensitive neurons. If we measure the amount of [$^3$H]-norepinephrine, [$^3$H]-dopamine or [$^3$H]-serotonin released to electrical stimulation from an isolated rat brain stem e.g. in a 3-min collection period and repeat the measurement in the presence of the optimal concentration of Deprenyl or BPAP, in which they exert their specific enhancer effect, the released amount of the labeled transmitter is significantly higher. This shows that the enhancer sensitive neuronal population, as a whole, works immediately on a higher activity level in the presence of the synthetic enhancer substance. After a single washout the neurons work immediately on their normal activity level again. Since neurons respond to stimulation in an "all or none" manner, it is obvious that only a part of the neuronal population (the most excitable ones) respond to the electrical stimulation. Since the enhancer substances amplifies the excitability of the neurons, in the presence of the enhancer substance a higher percentage of the neuronal population gets excited and the amount of the labeled transmitter released to the electrical stimulation is significantly increased (for review see Knoll, 2005, 3.1.3.).

The demonstration of the enhancer-sensitivity of such life important central nervous system regulations represented by noradrenergic, dopaminergic and serotonergic neurons in the brain stem; as well as the discovery that Deprenyl is a PEA-derived synthetic CAE-substance; initiated our first longevity study performed with low doses of Deprenyl in which they exert their "specific" and "non specific" enhancer effect. Since we demonstrated earlier that the enhancer regulation in the catecholaminergic and serotonergic systems in the rat brain is working on a significantly higher activity level from weaning until sexual maturity (Knoll and Miklya, 1995), and sexual hormones terminate in the rat the significantly enhanced catecholaminergic/serotonergic tone in the brain characteristic to the post-weaning period, we started the longevity study in sexually mature 2-month-old Wistar (Charles River) male rats in May 2010. This study revealed that a hitherto unknown enhancer-sensitive tumour manifestation suppression (TMS) regulation works in a mammalian brain. This finding form the basis of the subject of this patent specification.

The Present Longevity Study Revealed that a Hitherto Unknown Enhancer-Sensitive Tumor-Suppressing-Mechanism (TSM) Works in the Brain of Our Wistar Rats.

It is characteristic to our substrain of Wistar rats that a high percentage start to develop around the completion of the first year of their life a rapidly growing fibromyxosarcoma infiltrating the subcutaneous tissue including the muscles. We worked in our longevity study with males and observed that 50% of the animals developed the tumor during their lifetime. We experienced that the manifestation of the fibromyxosarcoma was significantly decreased in rats treated 3 times a week from the completion of the $2^{nd}$ month of their age with an enhancer substance [(−)-deprenyl (0.1 mg/kg) or (−)-BPAP (0.05 or 0.0001 mg/kg)]. In a group of 40 saline-treated (control) rats, the first animal manifested the tumor during the $11^{th}$ month of age and 20 rats in the group developed the tumor at the end of the $30^{th}$ month of their age. In contrast, in the group of 40 rats treated with 0.0001 mg/kg (−)-BPAP, the first rat that manifested the tumor was 20 months old and when this group of rats completed their $30^{th}$ month of life only 8 rats manifested the fibromyxosarcoma (P<0.001). In the group of 40 males treated with 0.05 mg/kg (−)-BPAP the first rat that manifested the tumor was 13 months old and when this group of rats completed their $30^{th}$ month of life only 7 rats manifested the tumor (P<0.001). In the group of 40 males treated with 0.1 mg/kg (−)-deprenyl, the first rat that manifested the tumor was 16 months old and when this group of rats completed their $30^{th}$ month of life only 11 rats manifested the tumor (P<0.01). Thus, even 0.0001 mg/kg (−)-BPAP was more potent in suppressing tumor manifestation than 0.1 mg/kg (−)-deprenyl.

Like the known enhancer effects of (−)-deprenyl and (−)-BPAP, the TMS effect too is a central effect.

Since the TMS regulation has nothing to do with a direct cytotoxic effect in tumor cells, we tested the effect of BPAP and Deprenyl in two types of human cultured medulloblastoma cell lines: Daoy HTB-186 cell line, originating from desmoplastic cerebellar medulloblastoma (Jacobsen et al. 1985) and UW-228-2 cell line, originating from posterior fossa medulloblastoma with a diploid DNA content (Keles et al. 1985). It is in harmony with the above conclusion that both (−)-deprenyl and (−)-BPAP did not inhibit the proliferation of human medulloblastoma cells in culture.

The Wistar rats are born with a sensitivity to manifest a rapidly growing fibromyxosarcoma infiltrating the subcutaneous tissue including the muscle. They are also born with an innate protective mechanism working against the manifestation of the tumor. Since Deprenyl and BPAP keep the TMS neurons on a higher activity level, they influence the manifestation of the fibromyxosarcoma accordingly.

Deprenyl is a PEA-derived synthetic enhancer of the catecholaminergic neurons; however Deprenyl is almost inactive on the serotonergic neurons. Using Deprenyl as the specific enhancer substances as exemplary experimental tool, we quite unexpectedly discovered the operation of an enhancer-sensitive TMS regulation in the rat brain. As expected, many aspects of the enhancer-sensitive regulations and the endogenous enhancer substances pertaining to these regulations are unknown. Enhancer-research is obviously in its pioneer stage.

To further study if BPAP would inhibit tumor growth and metastasis in vivo in another species, lung carcinoma formation has been tested in FVB/N mice (Taketo M. 1991) (see Example 3).

Below the Nature of the TMS Brain Regulation, the Mechanism of Action of the Enhancer Substances, and the Chance to Give Tumor-Research Another Course: Prevention is Further Discussed.

Collating the experiences regarding the enhancer effect of Deprenyl and BPAP on the enhancer-sensitive noradrenergic, dopaminergic, and serotonergic neuronal systems, the activity of which are on a continuous age-related decline, and the effect of the enhancer substances shown in FIG. 9-12, we may reasonably conclude, without being bound by theory, that a hitherto unknown enhancer-sensitive group of neurons exist in the rat brain the physiological function of which is the suppression of tumors for which the individual is predisposed. This is the first example of the existence of a highly efficient TMS mechanism in a mammalian brain.

It follows from prior art results that due to aging enhancer-sensitive neurons arrive to a critical threshold which leads to the manifestation of a pathological condition related to the system. For example, we know exactly that in the case of the enhancer-sensitive dopaminergic neurons the dopamine content in the striatum, due to the age-related decay of the system, is arriving to a critical level (30% of the normal level) when the symptoms of Parkinson disease (PD) appear, thus the disease is diagnosed.

It is common experience that regardless of method and species used for studying any type of performance, the observer encounters substantial differences in individual performance. Whatever function we measure, in every group of mammals we shall find lower and higher performing individuals. In case of the enhancer-sensitive regulations, we demonstrated in our longevity studies that with the administration of Deprenyl we change the lower performing individuals to better performing ones (Knoll, 1988; Knoll, Dalló, Yen, 1989; Knoll, Yen, Miklya, 1994).

All this is true for the enhancer-sensitive TMS mechanism. Since the preventive administration of the enhancer-substances in optimal doses keep the TMS system on a higher activity level, the manifestation of the first tumor is shifted and occurs later in time and a higher percentage of rats die before the decline of the activity of the TMS system is crossing the critical threshold and thus before the uninhibited proliferation of the tumor cells would start. For example, in this experiment the last animal in the saline-treated group of rats (N=40) died in the $32^{nd}$ month of its life. Half of the group (20 rats) died without manifesting the tumor. We may say that regarding the TMS function these rats were the high performing individuals. The other half of the rats (20 rats) developed the tumor before they died. Thus, in these rats the aging-related decline of the enhancer regulation in the TMS neurons crossed the critical threshold and we observed the manifestation of the fibromyxosarcoma. Keeping the TMS neurons on a higher activity level with the lifelong administration of, for example, 0.05 mg/kg BPAP slowed the aging-related decay of the enhancer regulation in the TMS neurons and 7 rats manifested the fibromixosarcoma (see FIG. 11).

Figure 13:
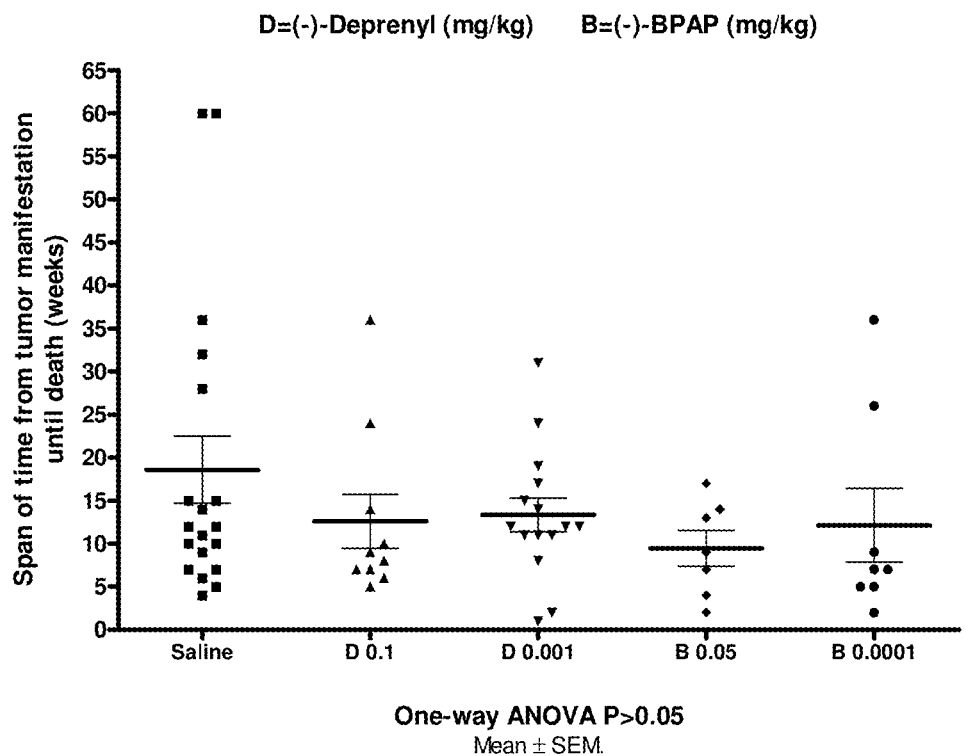
FIG. 13. Span of time from tumor manifestation until death in rats treated chronically with (−)-deprenyl and (−)-BPAP, respectively.

The enhancer substances reveal that a hitherto unknown enhancer-sensitive TMS mechanism is working in the brain. By the aid of the prophylactic administration of a synthetic enhancer substance we significantly increase the chances of the individual to avoid the manifestation of the tumor for which the strain is predisposed. There is no difference in the microscopy and histology of the fibromyxosarcomas developed in the saline- or enhancer-treated rats. Furthermore, FIG. 13 shows that there is no significant difference in the span of time from tumor manifestation until death in rats treated chronically with saline, Deprenyl or BPAP.

Table 2 shows that regarding the age-related changes in bodyweight there is no significant difference between saline-, or enhancer-treated rats.

TABLE 2

Aging-related changes of bodyweight (average in grams). Treatment started with two months old rats. Weight was measured four-weekly.

| Four week peri-ods | Saline | (−)-Deprenyl | | (−)-BPAP | |
|---|---|---|---|---|---|
| | | 0.1 mg/kg | 0.001 mg/kg | 0.05 mg/kg | 0.0001 mg/kg |
| 1 | 344 ± 14 | 348 ± 15 | 328 ± 22 | 289 ± 14 | 318 ± 19 |
| 2 | 507 ± 36 | 509 ± 36 | 504 ± 29 | 492 ± 28 | 513 ± 35 |
| 3 | 548 ± 38 | 552 ± 36 | 541 ± 33 | 531 ± 31 | 558 ± 47 |
| 4 | 581 ± 44 | 574 ± 38 | 568 ± 34 | 581 ± 39 | 609 ± 49 |
| 5 | 619 ± 48 | 617 ± 40 | 592 ± 47 | 614 ± 39 | 634 ± 49 |
| 6 | 649 ± 56 | 646 ± 51 | 640 ± 44 | 641 ± 43 | 659 ± 61 |
| 7 | 685 ± 67 | 689 ± 56 | 677 ± 51 | 686 ± 56 | 704 ± 63 |
| 8 | 735 ± 72 | 726 ± 71 | 689 ± 59 | 692 ± 60 | 746 ± 71 |
| 9 | 736 ± 70 | 726 ± 70 | 712 ± 74 | 723 ± 65 | 744 ± 68 |
| 10 | 834 ± 75 | 822 ± 81 | 825 ± 74 | 830 ± 68 | 849 ± 75 |
| 11 | 807 ± 80 | 779 ± 83 | 773 ± 68 | 788 ± 76 | 799 ± 77 |
| 12 | 807 ± 76 | 796 ± 77 | 800 ± 66 | 794 ± 74 | 819 ± 77 |
| 13 | 813 ± 76 | 806 ± 80 | 816 ± 71 | 791 ± 74 | 834 ± 83 |
| 14 | 831 ± 93 | 827 ± 80 | 704 ± 42 | 811 ± 76 | 843 ± 88 |
| 15 | 835 ± 92 | 749 ± 53 | 833 ± 90 | 808 ± 79 | 849 ± 84 |
| 16 | 853 ± 96 | 833 ± 80 | 842 ± 83 | 822 ± 81 | 853 ± 81 |
| 17 | 866 ± 93 | 846 ± 79 | 856 ± 89 | 831 ± 83 | 869 ± 79 |
| 18 | 861 ± 85 | 853 ± 82 | 850 ± 98 | 833 ± 82 | 873 ± 81 |
| 19 | 867 ± 84 | 851 ± 83 | 844 ± 94 | 828 ± 77 | 860 ± 78 |
| 20 | 866 ± 83 | 846 ± 85 | 845 ± 89 | 835 ± 75 | 859 ± 80 |
| 21 | 812 ± 78 | 820 ± 84 | 811 ± 82 | 824 ± 81 | 826 ± 86 |
| 22 | 798 ± 57 | 829 ± 85 | 825 ± 72 | 820 ± 59 | 828 ± 82 |
| 23 | 802 ± 63 | 825 ± 87 | 833 ± 81 | 828 ± 64 | 836 ± 81 |
| 24 | 795 ± 43 | 769 ± 62 | 796 ± 64 | 805 ± 48 | 790 ± 59 |
| 25 | 757 ± 38 | 749 ± 53 | 759 ± 35 | 772 ± 58 | 754 ± 58 |
| 26 | 697 ± 84 | 709 ± 70 | 703 ± 42 | 743 ± 79 | 710 ± 75 |
| 27 | 604 ± 96 | 660 ± 75 | 679 ± 59 | 732 ± 98 | 644 ± 141 |
| 28 | 663 ± 67 | 544 ± 76 | 626 ± 147 | 762 ± 64 | 611 ± 96 |
| 29 | 655 ± 60 | 579 ± 61 | 646 ± 142 | 689 ± 95 | 634 ± 61 |
| 30 | 603 ± 28 | 568 ± 38 | 542 ± 71 | 630 ± 125 | 588 ± 61 |
| 31 | 565 ± 25 | 560 ± 20 | 495 ± 15 | 565 ± 137 | 540 ± 67 |
| 32 | | 470 ± 0 | | 574 ± 46 | 590 ± 0 |

One-way Anova: P = 0.9624 (ns)

Since enhancer substances act in optimal concentrations highly specifically on enhancer-sensitive neurons in the brain, the ineffectiveness of BPAP and Deprenyl on the two human medulloblastoma cell lines strongly support our conclusion that in our strain of rats, susceptible to manifest a fibromyxosarcoma, a hitherto unknown enhancer sensitive regulation is operating which inhibits the manifestation of the tumor. Due to the aging-related decline of the enhancer regulation, the number of rats which manifest the tumor is continuously increasing with the passing of time. Maintenance on a proper dose of an enhancer substance keeps the enhancer-sensitive neurons on a higher activity level and a significantly lower number of rats manifest the tumor.

Preparation of enhancer compounds of the invention is described e.g. in the following patents and patent applications: WO1999007667A1, WO1988002254(A1).

Preferably, an enantiomerically pure compound is used.

Formulation of enhancer compounds of the invention is in general within the skills of a person skilled in the art. Usually the abundant guidance in connection with MAO inhibitors like selegilin can be followed with the exception that the dose is significantly lower and formulation should be adapted to this low dose.

Formulation variations of Deprenyl (selegiline) are for example well-known in the art [see e.g. Clarke A et al. J Neural Transm. 2003 November; 110(11):1257-71. A new low-dose formulation of selegiline: clinical efficacy, patient preference and selectivity for MAO-B inhibition; Fowler, Joanna S., Evidence that Formulations of the Selective MAO-B Inhibitor, Selegiline, which Bypass First-Pass Metabolism, also Inhibit MAO-A in the Human Brain; Neuropsychopharmacology advance online publication 29 Oct. 2014; doi: 10.1038/npp.2014.214].

In general, low dose, buccal and fast dispersing, and retard formulations are well known in the art and can be applied herein according to patient requirements.

Specifically, about the preparation of low dose medicaments an abundant teaching can be found in the following publications: [Ahmed H, Shah N. (2000) Formulation of low dose medicines—theory and practice. Am. Pharm. Rev. 3(3): 9-14; Jack Zheng (2009) Formulation and Analytical Development for Low-Dose Oral Drug Products. John Wiley & Sons]

The invention is further described by way of examples herein. It should be noted that the examples have an exemplary and illustrative nature and the description of the invention involves the whole teaching provided herein.

EXAMPLES

Example 1—Longevity Studies in Rat Model with (−)Deprenyl and (−)BPAP Reference Compound)

Materials and Methods
Materials
(−)1-(Benzofuran-2-yl)-2-propyl-aminopentane HCl [(−)BPAP] Fujimoto Pharmaceutical Corp., Osaka, Japan; (−)Deprenyl (Selegiline), Sanofi-Chinoin, Budapest, Hungary; Tetrabenazine HCl (synthesized by Prof. C. Szántay, Department of Organic Chemistry, University of Technical Sciences, Budapest, Hungary).

Animals

Experiments were carried out on male Wistar rats (Charles River) weighing 250-350 g received from the breeding colony of Semmelweis University. The animals were kept in a 12-hour light-dark cycle and under condition of controlled temperature (22±2° C.) and relative humidity (55±5%). Room temperature and relative humidity was checked daily. The rats were maintained on standard laboratory chow and tap water ad libitum. All procedures conformed to the European Convention for the protection of vertebrate animals used for experimental and other scientific purposes. The study was approved by the Animal Ethics Committee of Semmelweis University, Budapest (permission number: 1810/003/2004)

The Selection of the Proper CAE Doses of Deprenyl and BPAP for the Longevity Study Through Shuttle Box Experiments In a modified version of the shuttle box the acquisition of a two-way conditioned avoidance reflex (CAR) was analyzed during 5 consecutive days. The rat was put in a box divided inside into two parts by a barrier with a small gate in the middle, and the animal was trained to cross the barrier under the influence of a conditioned stimulus (CS, light flash). If it failed to respond within 5 s, it was punished with a foot-shock (1 mA), the unconditioned stimulus (US). If the rat failed to respond within 5 s to the US, it was classified as an escape failure (EF). One trial consisted of 10 s intertrial interval, followed by 20 s CS. The last 5 s of CS overlaped the 5 s US. At each learning session, the number of CARs, EFs and intersignal reactions (IRs) are automatically counted and evaluated by multi-way ANOVA.

Tetrabenazine-treatment (1 mg/kg s.c.) depletes at least 90% of norepinephrine and dopamine from their stores in the nerve terminals of the catecholaminergic neurons in the brain stem. Due to the weak performance of the catecholaminergic brain engine, the activation of the cortical neurons remains below the level required for the acquisition of a CAR. The learning deficit caused by tetrabenazine-treatment can be antagonized by the administration of a synthetic CAE substance or an A-type MAO inhibitor, whereas selective inhibition of B-type MAO or inhibition of the reuptake of catecholamines and/or serotonin is ineffective (Knoll et al., 1992).

The enhancer substances exert their enhancer effect with a peculiar dose-dependency: a bi-modal, bell-shaped concentration effect curve is characteristic to the enhancer effect. BPAP enhanced the activity of the noradrenergic neurons in the femto/picomolar concentration range ("specific enhancer effect"), and also in a 10 million times higher concentration range ("non-specific enhancer effect"). Deprenyl is a less potent CAE-substance than BPAP, but otherwise it exerts its specific and non-specific enhancer effect with the same characteristics as BPAP (Knoll et al., 1999, Knoll, Miklya, Knoll B, 2002).

Figure 3:
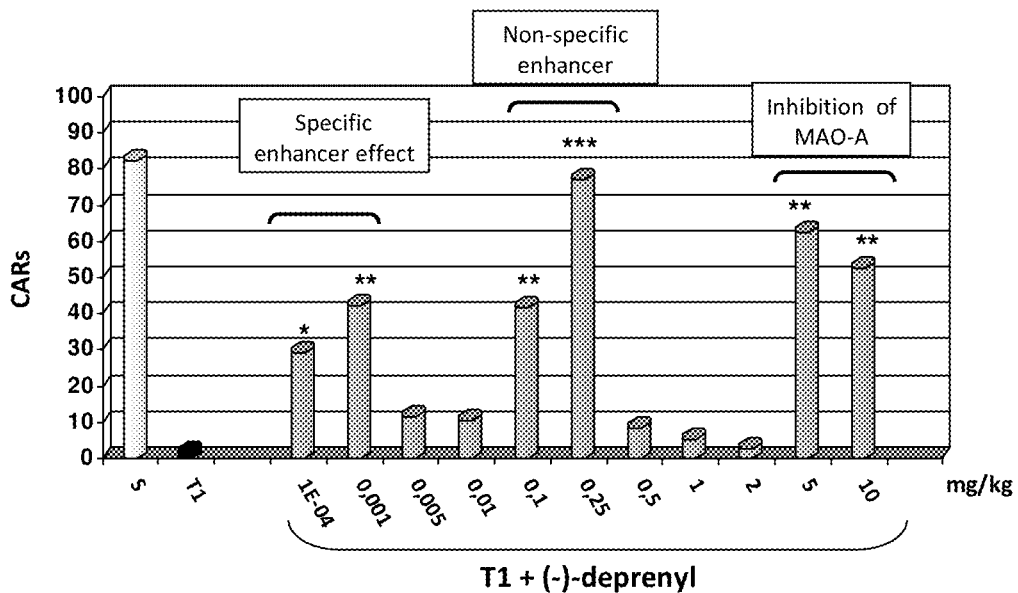
FIG. 3. Selection of optimal doses of (−)-deprenyl for the longevity study in the shuttle box. Measured: (S) the ability of saline-treated (control) rats to fix conditioned avoidance responses (CARs); (Ti) the inhibition of the learning ability of rats treated subcutaneously with 1 mg/kg tetrabenazine, one hour prior to training; [Ti+(−)-deprenyl] the ability of (−)-deprenyl to antagonize in a dose related manner the inhibitory effect of tetrabenazine. Significance in the performance between the groups was evaluated by multi-factor analysis of variance (ANOVA). *P<0.05; P<0.01; *P<0.001

FIG. 3 shows that in this in vivo test too, a bi-modal, bell-shaped dose-effect-relation characterizes the enhancer effect of D. We selected for the longevity study two doses of Deprenyl, 0.001 mg/kg and 0.1 mg/kg. The 0.001 mg/kg was selected as the optimal dose that exerted the specific enhancer effect. Regarding the dose with the non-specific enhancer effect, the less effective 0.1 mg/kg dose was selected for the longevity study because it allows B-type MAO to sufficiently oxidize the proper monoamines. The figure also shows that very high doses of Deprenyl (5-10 mg/kg), due to the inhibition of MAO-A, are effective in antagonizing the tetrabenazine-induced learning deficit.

Figure 4:
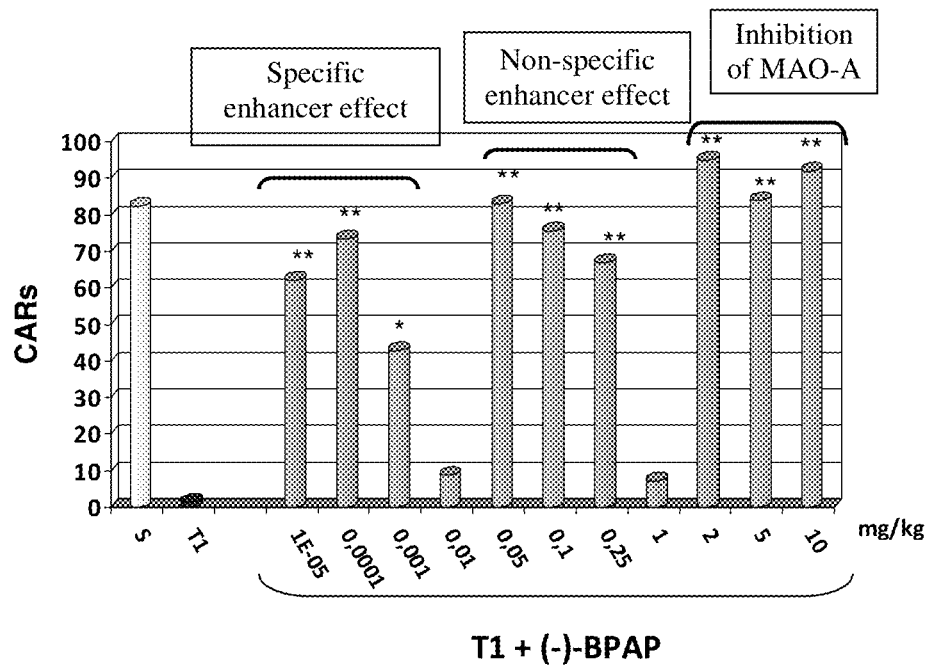
FIG. 4. Selection of optimal doses of (−)-BPAP for the longevity study in the shuttle box. Measured: (S) the ability of saline-treated (control) rats to fix conditioned avoidance responses (CARs); (Ti) the inhibition of the learning ability of rats treated subcutaneously with 1 mg/kg tetrabenazine, one hour prior to training; [Ti+(−)-BPAP] the ability of (−)-BPAP to antagonize in a dose related manner the inhibitory effect of tetrabenazine. Significance in the performance between the groups was evaluated by multi-factor analysis of variance (ANOVA). *P<0.01; **P<0.001

FIG. 4 shows the dose-related effect of BPAP in the shuttle box. For the longevity study we selected the optimal dose that elicited the specific (0.0001 mg/kg) and the non-specific (0.05 mg/kg) enhancer effect. Since BPAP blocks the activity of MAO-A in higher than 2 mg/kg dose (Knoll et al., 1999), it antagonized the tetrabenazine-induced learning deficit in the extremely high dose-range (2-10 mg/kg).

The fact that 0.0001 mg/kg BPAP is antagonizing the tetrabenazine-induced learning deficit in the shuttle box (FIG. 4) is undeniably primary in vivo evidence for the unique mechanism through which the enhancer substances rev up the catecholaminergic brain engine. In optimally low doses of PEA and Deprenyl, as well as, tryptamine and BPAP, there is an increase in the excitability of enhancer-sensitive neurons, thus we measured the enhancement of the impulse propagation mediated release of the transmitters from the catecholaminergic and the serotonergic neurons in the brain. In low doses Deprenyl is a selective CAE-substance. BPAP, preferentially a serotonergic activity enhancer substance, is even as a CAE substance a much more potent enhancer than D.

Longevity Study

The longevity study was performed on 200 male rats received from the breeding colony of the Semmelweis University. The rats were born at the end of February of 2010. After 2-month acclimation period the rats were divided randomly into 5 even groups. The longevity study started at the beginning of May 2010. Animals were observed until their natural deaths. The data in this study represent the changes observed until Oct. 31, 2012, since in the saline-treated group the last animal died on Oct. 31, 2012. As will be shown later a few rats in the enhancer-treated groups were still alive on Nov. 1, 2012.

During the longevity study 5 rats were housed together in polycarbonate cages (height: 18 cm; wide: 42 cm; length: 44 cm) with a stainless steel on the top. Cage bedding was renewed 3 times a week (Monday, Wednesday and Friday). Bodyweight was measured once every month. The treatment started at the end of the second month of their age. Saline, (−)-deprenyl and (−)-BPAP, respectively were injected subcutaneously 3 times a week (Monday, Wednesday, Friday). The treatment of the five groups of rats participating in the longevity study is shown in Table 3. To avoid the mixing of the groups and individuals, saline-treated rats were signed blue from 1 to 40; D-treated rats were signed green from 1 to 80 (1-40: rats treated with 0.1 mg/kg and 41-80: rats treated with 0.001 mg/kg); B-treated rats were signed black from 1 to 80 (1-40: rats treated with 0.05 mg/kg and 41-80: rats treated with 0.0001 mg/kg).

TABLE 3

Treatment on Wistar male rats participating in the longevity study.

| Group | Treatment | Dose | Number of animals |
|---|---|---|---|
| 1 | Saline | 0.5 ml/kg | 40 |
| 2 | (−)-Deprenyl | 0.1 mg/kg | 40 |
| 3 | (−)-Deprenyl | 0.001 mg/kg | 40 |
| 4 | (−)-BPAP | 0.05 mg/kg | 40 |
| 5 | (−)-BPAP | 0.0001 mg/kg | 40 |

Observation of Tumors

We carefully observed the appearance of the subcutaneous tumor and followed the development of the tumor until death. Histological analysis was performed post mortem on several rats taken from each group as examples.

The subcutaneous tumors developed in the rats were measured by the two largest diameters. After sacrificing the animals, the tumors were removed, photographs were taken. Tissues were fixed immediately after removal in 10% neutral formalin (in PBS, pH7.0) for 24 hours at room temperature, dehydrated and embedded in paraffin. 3-4 micrometer thick sections were cut and stained by hematoxylin and eosin (HE) as a routine.

The tumors were white-greyish, of soft consistency. Occasionally hemorrhagic and necrotic areas of various degree could be detected. Histologically the tumor cells were round or elongated with roundish or oval nuclei and eosinophilic cytoplasm. Occasionally mitotic figures were seen. The cells were embedded in a pale partly eosinophilic, partly basophilic loose matrix which contained areas of collagen fibers. The tumor infiltrated the subcutaneous tissues and the striated muscles.

To prove the origin of the tumors, immunohistochemical reactions were carried out on formalin-fixed, paraffin embedded sections. Following deparaffinization and rehydrations the slides were incubated by the following primary antibodies against vimentin (Dako, Glostrup, Denmark, 1:1200 dilution), smooth muscle antibodies (SMA, Dako, 1:400 dilution), desmin (Dako, 1:300 dilution), Ki67 (Dako, 1:100 dilution). The reactions were carried out in a Ventana Benchmarck XT automated immunohistochemical staining system (Ventana Medical System Inc., Tucson, Ariz., USA) with HRP Multimer based, biotin-free detection method. Reagents and secondary antibodies were obtained from Ventana (iView DAB Detection Kit, Ventana).

Immunohistochemistry proved the mesenchymal origin of the tumor cells, which stained strongly with vimentin, however reactions for SMA and desmin were negative. Ki67 was positive in up to 5% of the tumor cells, indicating the proliferation of the tumor cells.

The final histological diagnosis was fibromyxosarcoma in the subcutaneous tissue.

Results of Longevity Studies

The lifespan prolonging effect of low doses of Deprenyl and BPAP in which they exert their "specific" and "non-specific" enhancer effect In our two longevity studies with Deprenyl performed before the discovery of the CAE effect of the drug, we used the 0.25 mg/kg dose of Deprenyl which completely blocks MAO-B activity in the brain. In this study, we used the peak doses of Deprenyl in which the compound exerted in the Shuttle box experiment its "non-specific" and "specific" enhancer effect (see FIG. 3).

The first animal in the saline-treated group died in the $9^{th}$ month of its age and the last animal died in the $32^{nd}$ month of its age.

Figure 5:
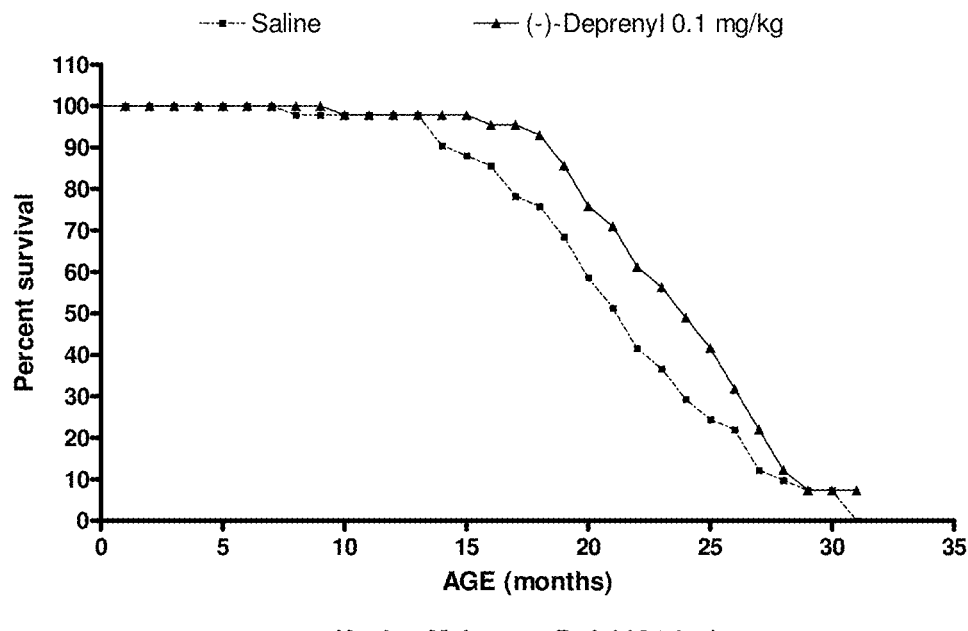
FIG. 5. Influence of chronic treatment with 0.1 mg/kg (−)-deprenyl on survival. (N=40)
Figure 6:
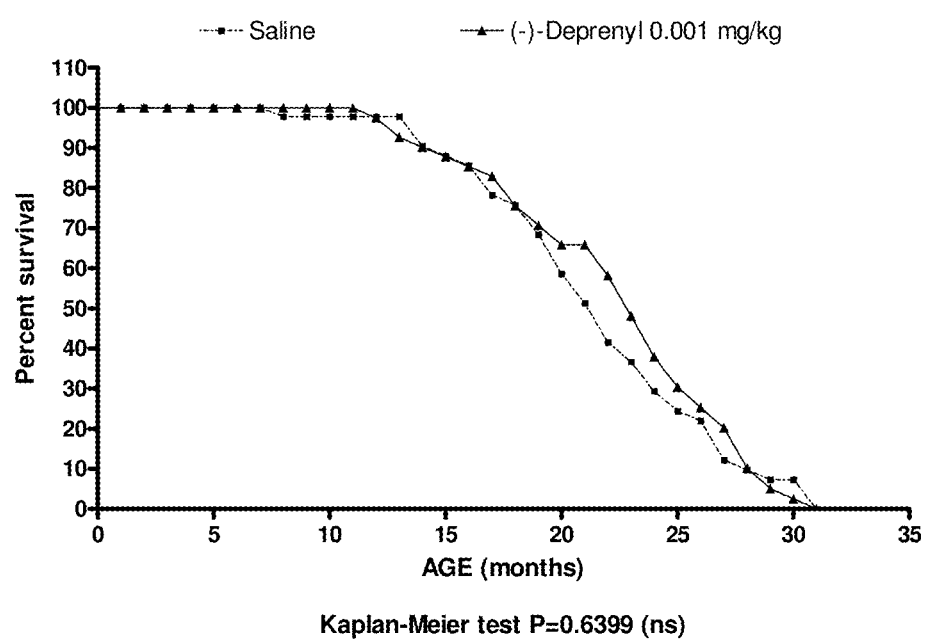
FIG. 6. Influence of chronic treatment with 0.001 mg/kg (−)-deprenyl on survival. (N=40)

FIG. 5 shows that in the group of rats treated with 0.1 mg/kg Deprenyl the first animal died in $11^{th}$ month of its age and 2 rats remained alive to the end of the $32^{nd}$ month of their age (P>0.05). FIG. 6 shows that in the group of rats treated with 0.001 mg/kg Deprenyl the first animal died in the $13^{th}$ month of its age and none of the rats remained alive to the end of $32^{nd}$ month (P>0.05).

Though according to FIGS. 5 and 6 Deprenyl did not prolong the lifespan of rats significantly, a change in this direction is obvious. B-treated rats lived, however, significantly longer than their saline-treated peers.

Figure 7:
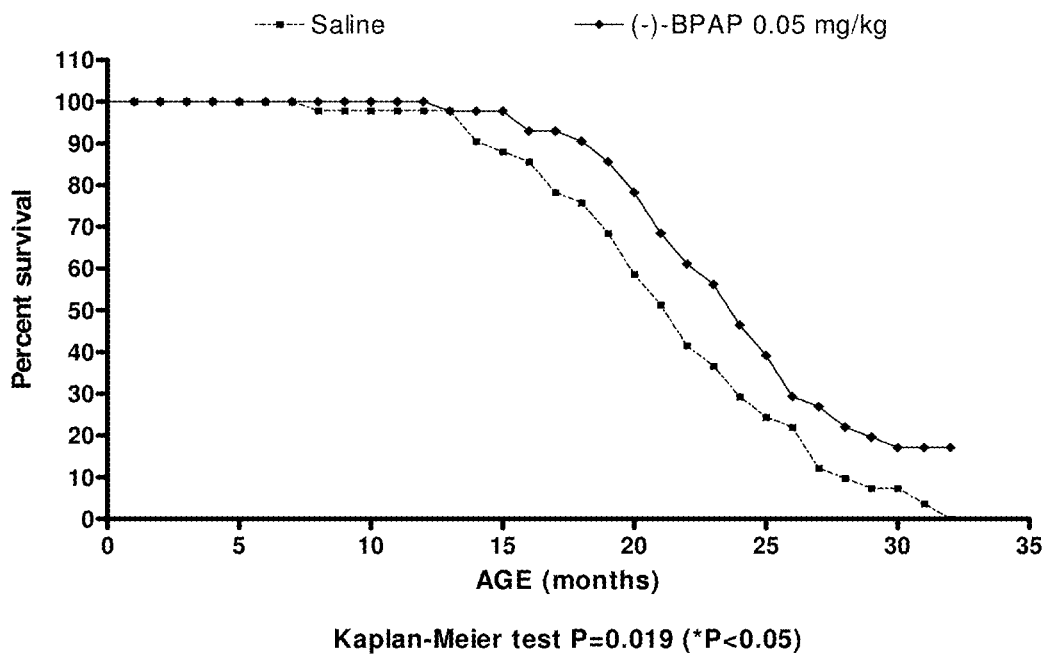
FIG. 7. Influence of chronic treatment with 0.05 mg/kg (−)-BPAP on survival. (N=40)
Figure 8:
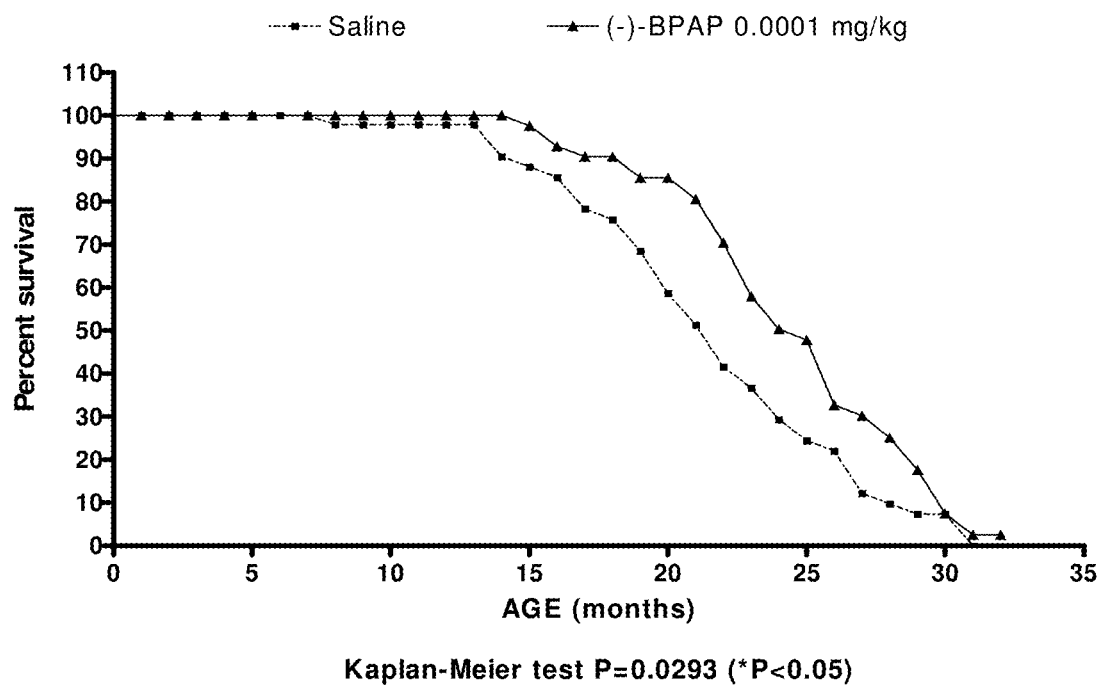
FIG. 8. Influence of chronic treatment with 0.0001 mg/kg (−)-BPAP on survival. (N=40)

FIG. 7 shows that in the group of rats treated with 0.05 mg/kg BPAP the first animal died in the $14^{th}$ month of its age and 5 rats remained alive to the end of the $32^{nd}$ month of their age (*P<0.05). FIG. 8 shows that in the group of rats treated with 0.0001 mg/kg BPAP the first animal died in the $16^{th}$ month of its age and one rat remained alive to the end of $32^{nd}$ month of its age (*P<0.05).

The Tumor-Manifestation-Suppressing (TMS) Effect of Deprenyl and BPAP

In the Course of Our Longevity Study we Discovered that a Peculiar, Previously Unknown Enhancer-Sensitive TMS Mechanism is Operating in the Brain of Our Rats.

It belongs to the natural endowments of the Wistar rats (Charles River) that around the completion of the first year of their life a rapidly growing fibromyxosarcoma, infiltrating the subcutaneous tissue including the muscles, starts to appear, the number of tumor manifesting rats is increasing with the passing of time, and finally about half of the population dies with the fibromyxosarcoma.

In our running longevity study the first animal manifested the tumor in the saline-treated group of rats during the 11$^{th}$ month of age and 20 rats in the group manifested the tumor to the end of 27$^{th}$ month of their age. The last two animals in this group died during the 32$^{nd}$ month.

Figure 9:
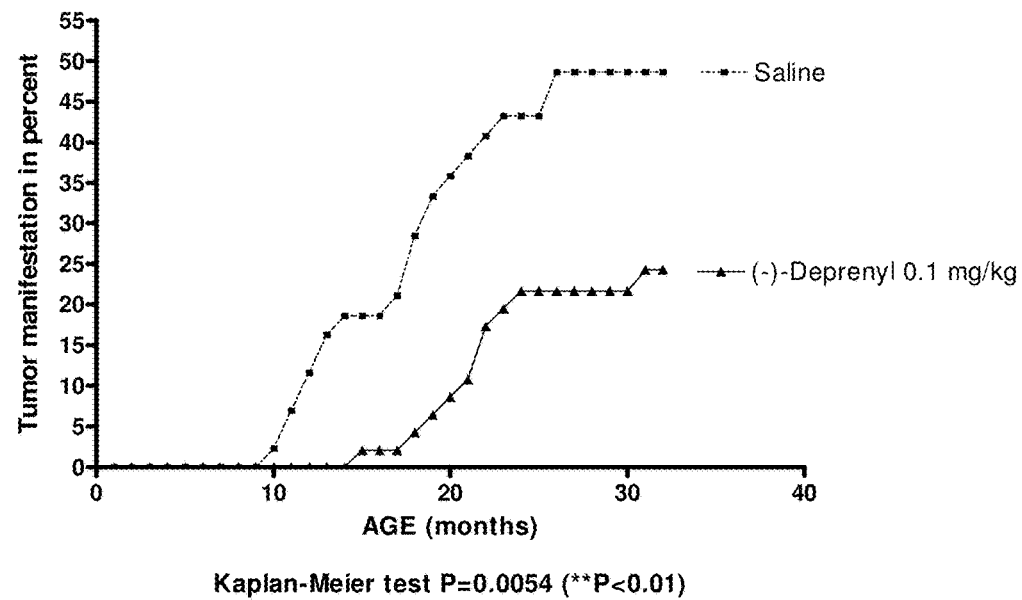
FIG. 9. The tumor manifestation suppressing effect of chronic treatment with 0.1 mg/kg (−)-deprenyl. (N=40)

In the group of rats treated with 0.1 mg/kg Deprenyl the first animal manifested the tumor during the 16$^{th}$ month of age and 11 rats in the group manifested the tumor to the end of the 32$^{nd}$ month of age. The last animal manifested the tumor during the 32$^{nd}$ month. Two rats in this group are still alive. FIG. 9 shows that treatment of rats with 0.1 mg/kg Deprenyl suppressed the manifestation of the fibromyxosarcoma significantly ($P<0.01$).

Figure 10:
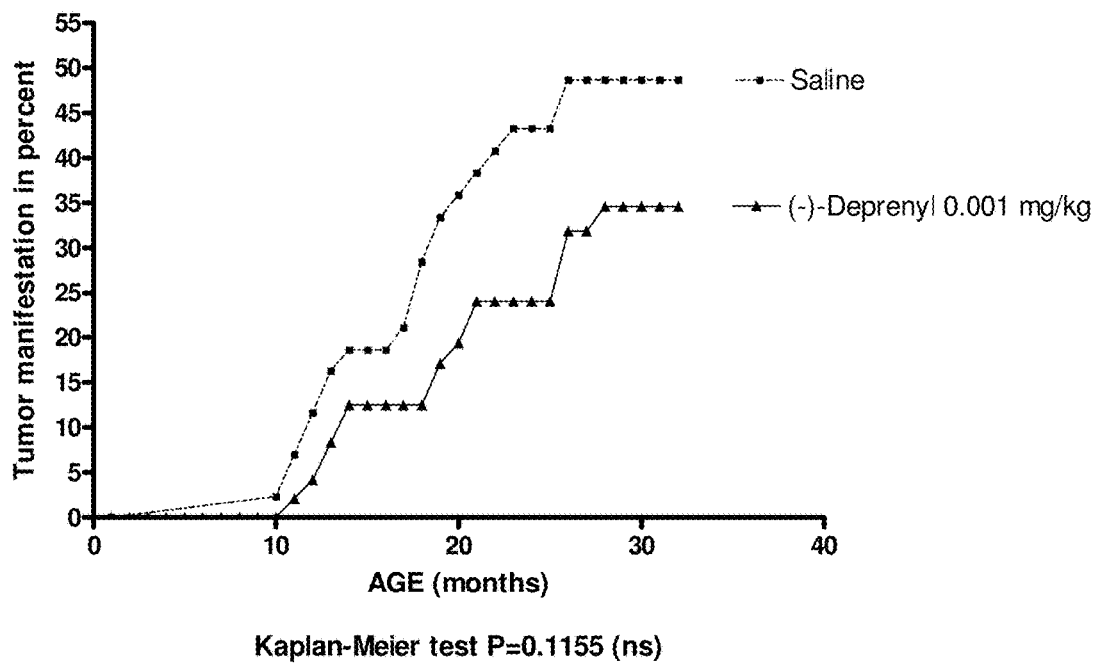
FIG. 10. The tumor manifestation suppressing effect of chronic treatment with 0.001 mg/kg (−)-deprenyl. (N=40)

In the group of rats treated with 0.001 mg/kg Deprenyl the first animal manifested the tumor during the 12$^{th}$ month of age and 15 rats in the group manifested tumors at the end of the 32$^{nd}$ month of age. The last animal manifested the tumor during the 29$^{th}$ month. The last animal in this group died during the 32$^{nd}$ month of its age. FIG. 10 shows that although the TMS effect of 0.001 mg/kg Deprenyl was not significant, the tendency is undeniable.

Figure 11:
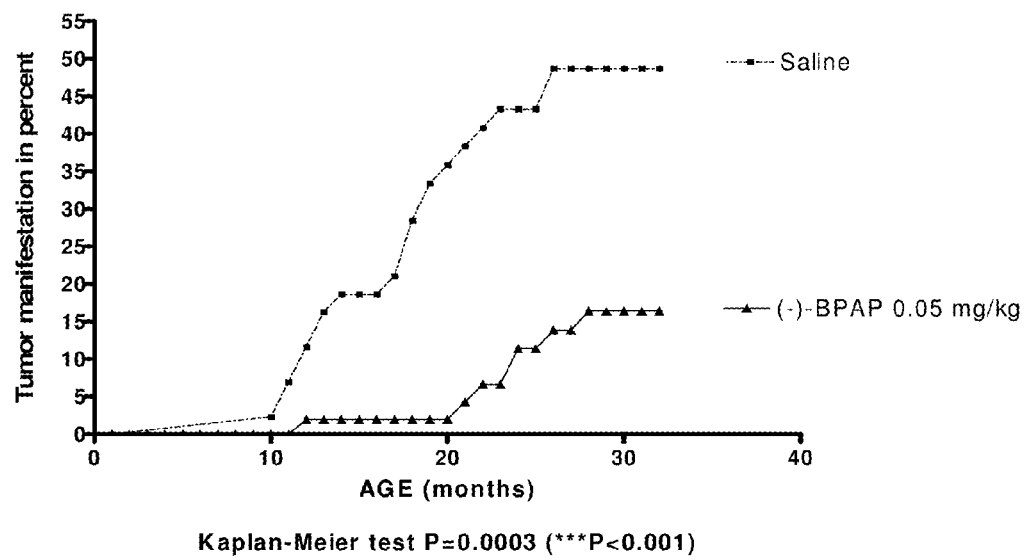
FIG. 11. The tumor manifestation suppressing effect of chronic treatment with 0.05 mg/kg (−)-BPAP. (N=40)

In the group of rats treated with 0.05 mg/kg BPAP the first animal manifested the tumor during the 13$^{th}$ month of age and 7 rats in the group manifested tumors at the end of 32 month of age. The last animal manifested the tumor during the 29$^{th}$ month of its age. Five rats in this group are still alive. FIG. 11 shows that treatment of rats with 0.05 mg/kg BPAP suppressed the manifestation of the fibromyxosarcoma significantly ($P<0.001$).

Figure 12:
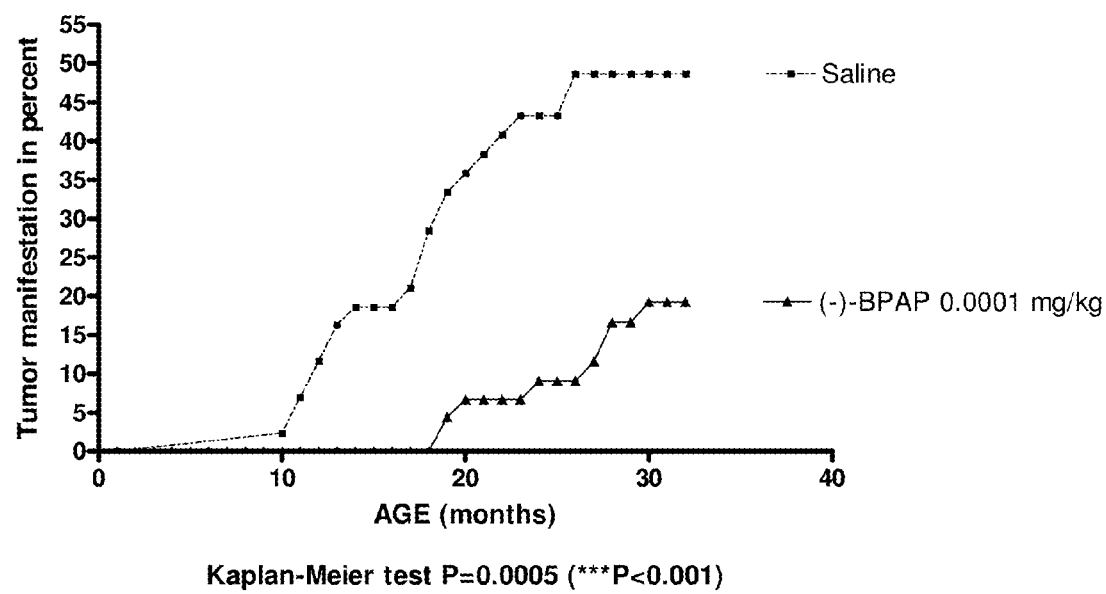
FIG. 12. The tumor manifestation suppressing effect of chronic treatment with 0.0001 mg/kg (−)-BPAP. (N=40)

In the group of rats treated with 0.0001 mg/kg BPAP the first animal manifested the tumor during the 25$^{th}$ month of age and 8 rats in the group manifested tumors at the end of 32 month of age. The last animal manifested the tumor during the 31$^{st}$ month. One rat in this group is still alive. FIG. 12 shows that treatment of rats with 0.0001 mg/kg BPAP suppressed the manifestation of the fibromyxosarcoma significantly ($P<0.001$).

Description of the Tumors
Macroscopy
Firm tumors appeared in subcutaneous localization in the rats. Photos have been made to illustrate the typical subcutaneous localization of the fibrosarcomas.

The tumors were well circumscribed, however, no detectable capsule could be seen. Photos have been made to illustrate the cut surface of the tumors was greyish-white, with no specific structures. Occasionally small hemorrhagic areas and yellow homogeneous necrotic areas could be seen.

Histology
On hematoxylin-eosin (HE) stained section, the tumor cells were located in a loosely arranged pale, eosinophilic matrix with large number of small vessels. The tumor cells had elongated or stellate forms with centrally or excentrically located roundish nuclei and pale eosinophilic cytoplasm. Occasionally mitotic figures were detected. On PAS reaction, the matrix gave a pale positive reaction, the tumor cells were mainly negative. Photos have been made to show the typical histology of the subcutaneous tumors.

Immunohistochemistry
By immunohistochemical reaction, the tumor cells stained strongly positive for vimentin. Antibody for SMA (smooth muscle antigen) stained only the vessels, the tumor cells were negative. Anti-desmin antibodies reacted with muscle components only which were infiltrated by the negatively stained tumor cells. H-caldesmon reaction was negative.

The Data Furnish Experimental Evidence that with the Passing of Time a Continuosly Increasing Percentage of the Wistar Rats Used in Our Study Develop a Rapidly Growing Subcutaneous Fibromyxosarcoma and it Seems Evident that the Manifestation of this Tumor Belongs to the Natural Endowments of this Strain.

Example 2—Experiments on Human Cultured Medulloblastoma Cell Lines

Cell Lines
Human medulloblastoma cell line, Daoy was purchased from ATCCC, UW-228 was obtained from the courtesy of Professor Silber (University of Washington, Seattle, Wash., USA).

Maintenance
Daoy and UW-228-2 cell lines were maintained in culture medium (each 500 ml Minimum Essential Medium Eagle, Alpha Modification (M8042, Sigma, St Louis, USA) with 50 ml FCS (Gibco), 40 mg Gentamicin (Sandoz), 5 ml sodium-pyruvate (S8636, Sigma, St Louis, USA), 5 ml non-essential-amino acid solution (M7145, Sigma, St Louis, USA), 10 ml L-glutamin (Sigma, St Louis, USA) at 37° C. in humified 5% $CO_2$.

Proliferation Assays
In each well $3\times10^3$ Daoy or UW-228-2 cells were seeded in 96-well plates (Sarstedt), solved in 100 l of its own medium with 10% FCS. 24 hours after seeding, cells were treated for 72 hours by drugs solved in further 100 μl medium. First, both cell lines were treated by (−)-BPAP and (−)-deprenil in monotherapy to determine its dose-effect curves in concentration of $10^{-6}$, $10^{-7}$, $10^{-1}$, $10^{-9}$, $10^{-10}$, $10^{-11}$, $10^{-12}$, $10^{-13}$ and $10^{-14}$ M. In combined treatment $10^{-3}$, $3.3\times10^{-4}$, $1.1\times10^{-5}$ and $3.7\times10^{-5}$ M of temozolomide (Schering Plough, USA) or 0.04, 0.2, 1, 5 μM of Cisplatin (Ebewe Pharma, Austria) or 0.04, 0.2, 1, 5 μM of etoposide (Ebewe Pharma, Austria) or $10^{-7}$, $10^{-6}$, $10^{-5}$ and $10^{-4}$ μM (UW228-2) or 0.001, 0.005, 0.025 and 0.125 μM (Daoy) of Vincristin (Richter Gedeon, Hungary) were applied in monotherapy or combined with $10^{-13}$ or $10^{-8}$ M of (−)-BPAP or (−)-deprenil.

Cell proliferation was evaluated by MTT (3-(4,5-Dimethylthiazol-2-yl)-2,5-diphenyltetrazolium bromide) assay (M5655, Sigma) after 72-hour treatment by the method described in manufacturer's protocol.

Statistics
Significance in the performance between the groups in the shuttle box was evaluated by multi-factor analysis of variance (ANOVA). Significance regarding the span of time from tumor manifestation until death in rats and regarding aging related changes in bodyweight treated chronically with the enhancer substances was analyzed by One-way ANOVA. Statistical analysis of survival rate and tumor manifestation was performed by the Kaplan-Meier method.

Results of Experiments on Human Cultured Medulloblastoma Cell Lines
We tested the effect of the enhancer substances in two types of human cultured medulloblastoma cell lines: Daoy HTB-186 cell line, originating from desmoplastic cerebellar medulloblastoma (Jacobsen et al., 1985), and UW-228-2 cell line, originating from posterior fossa medulloblastoma with a diploid DNA content (Keles et al., 1985), and investigated the effect of Deprenyl and BPAP, within the range between $10^{-14}$ and $10^{-6}$M, in nine concentrations. In none of the applied concentrations did Deprenyl or BPAP influence the proliferation on the cultured medulloblastoma cells. Moreover, BPAP and Deprenyl did not change the effectiveness of the investigated well-known tumor-cell proliferation inhibiting agents (see the investigated combinations in Methods).

The Ineffectiveness of the Enhancer Substances on the Proliferation of Cultured Tumor Cells is Congruent with the Physiological Function of the Enhancer-Sensitive TMS Regulation.

Example 3—Longevity Study on FVB/N Mice—Suppression of Spontaneous Lung Carcinoma Manifestation To examine the effect of (−)-deprenyl and (−)-BPAP on the lifespan of mice and autopsy made on randomly selected mice treated with doses in which they exert their "specific" (low, i.e. specific enhancer dose) and "non-specific" (higher, i.e. non-specific enhancer dose) enhancer effect; and the detection of the manifestation of lung carcinoma on randomly selected mice sacrificed at 6-month, 1-year, 1.5-year and 2-year time points.

Methods

Five groups of mice are treated daily from sexual maturity with two different doses of (−)-deprenyl and (−)-BPAP, respectively.
Group 1: Control: Saline
Group 2: BPAP low dose: 0.0001 mg/kg (−)-BPAP
Group 3: BPAP high dose: 0.05 mg/kg (−)-BPAP
Group 4: Deprenyl low dose: 0.001 mg/kg (−)-deprenyl
Group 5: Deprenyl high dose: 0.1 mg/kg (−)-deprenyl A total of 172 mice entered the experiments. Body weight is measured bimonthly.

For monitoring, we planned to sacrifice mice from each group at 6-month, 1-year, 1.5-year and 2-year time-points; the rest of the animals are kept until spontaneous death.

Results

The longevity study is still running; until the time being (November, 2015) the autopsy has been made of the 6-month, 1-year, 1.5-year treated mice. No lung carcinoma was detected in the 6-month or 1-year saline-treated mice. However, in 75% of the 1.5-year-saline-treated mice the tumor was detectable, whereas the tumor appearance was significantly lower or totally absent in the 1.5-year old enhancer-treated mice.

The results are shown in Table 4 and on FIGS. 19 and 20. Significance levels were calculated with two-sided Chi-square test.

TABLE 4

Results of the autopsy of mice after 18-month daily treatment with saline and enhancer substances, respectively

| Treatment | Number of dissected mice | Number of detected lung carcinoma |
|---|---|---|
| Saline | 4 | 3 |
| (−)-Deprenyl 0.1 mg/kg | 4 | 1 |
| (−)-Deprenyl 0.001 mg/kg | 2 | 0 |
| (−)-BPAP 0.05 mg/kg | 4 | 1 |
| (−)-BPAP 0.0001 mg/kg | 4 | 0 |

Table 4 shows that none of the 18 months old dissected mice, treated with specific enhancer dose, have developed lung carcinoma.

Figure 14:
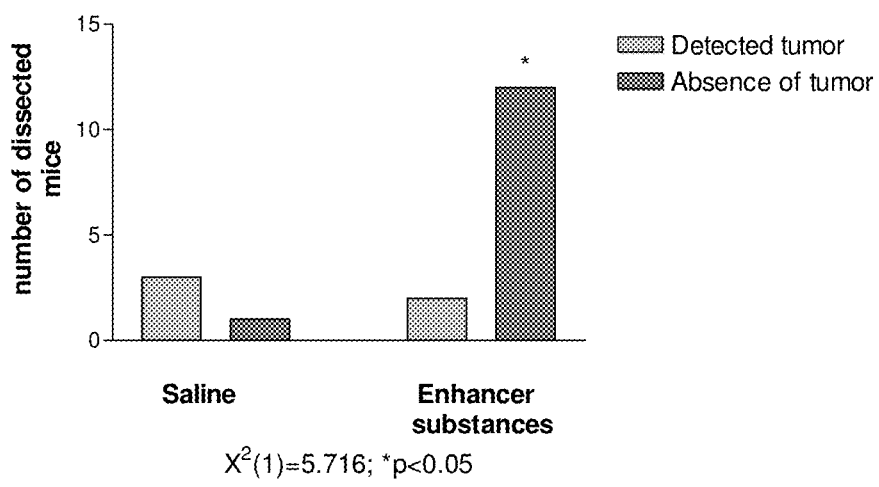
FIG. 14. Suppression of lung carcinoma manifestation in FVB/N mice treated for 1.5-year with enhancer substances, (−)-deprenyl and (−)-BPAP.

FIG. 14 shows the result of the calculation of significance between the four saline-treated mice and the total of 14 mice treated daily with enhancer substances for 18 month as shown in Table 4.

FIG. 15. shows that the extremely low dose of (−)-BPAP, which exerts its specific enhancer effect completely prevented the manifestation of lung carcinoma in FVB/N mice.

Example 4—Measurement of Monoamine Neurotransmitters Released from the Rat Brain Stem by Electrostimulation (Reference Example)

This measurement can be made, mutatis mutandis, analogously to the measurement described in example 2 of EP1052259B1 (corresponding to WO2000026204A1). The method is described in [Knoll J, Knoll B and Miklya I Life Sci, 58, 2101-2114 (1996)].

In short the brain stem (average weight about 800 mg) is isolated from rats and soaked in oxygenated Krebs' solution. Then solution of labelled neurotransmitter the release of which is measured is added to the preparation and allowed for uptake in an appropriate environment. If needed, MAO activity is inhibited.

After uptake of the monoamine the brain stem is fixed in appropriate organ bath and washed in appropriate solution facilitating uptake and preventing metabolization of the monoamine.

Fractionation of the perfusate is carried out periodically and, if the monoamine is radiolabelled, fractions are combined with a scintillation liquid.

The compound(s) of the invention are solved in perfusate buffer at enhancer concentration. As a (negative) control, the perfusate buffer or an appropriate buffer not comprising the compound can be used. As a positive control a compound with a known enhancer effect can be used.

If the curve typical of enhancer effect (typically a bimodal curve) is to be taken solutions of different concentrations spanning the possible concentration ranges are prepared.

The organ is perfused with the buffer containing the compound(s) of the invention for sufficient time before electrostimulation.

The brain stem is stimulated with rectangular pulses (e.g. 3 Hz, 1 ms 60 V) e.g. for 3 min. At the beginning of the experiment, the several, e.g. three resting periods of fraction were proceeded prior to the first stimulation. Thereafter it is allotted several, e.g. seven resting periods of fraction between stimulation.

The compound of the invention is confirmed to enhance the monoamine neurotransmitter release by the increase of the exocytosis, when electrostimulation was given to the neuronal cells.

Results

If a low dose or a minimum dose of the compound of the invention, causing release of the monoamine neurotransmitter from the electric-stimulated brain (e.g. brain-stem), is to be defined, the minimum dose of an enhancer compound is lowever than that of a MAO inhibitor, in particular significantly lower, typically below 0.04 or 0.02 µg/ml or even more preferably not higher or lower than 0.015 µg or 0.01 µg/ml.

If a concentration series spanning a range is applied, typically a bimodal curve of released monoamine amounts, as a function of the concentration of the inventive compound, is obtained. However, at least a bell-shaped curve is obtained in a low concentration range typical of the enhancer effect. Typically the medium of this curve is below 0.04 or 0.02 µg/ml or even more preferably not higher or lower than 0.015 µg or 0.01 µg/ml.

Example 5—Measurement of Biogenic Amines Released from Brain Tissue

This measurement can be made, mutatis mutandis, analogously to the measurement described in example 4 of EP1052259B1 (corresponding to WO2000026204A1). The method is described in [Knoll J, Knoll B and Miklya I Life Sci, 58, 2101-2114 (1996)].

Brain tissues (such as striatum, substantia nigra, tuberculum olfactorium, locus coeruleus and raphe) isolated from rats, e.g. Wistar rats are soaked in oxygenated Krebs' solution at body temperature. The preparations are submerged in organ bath, incubated for appropriate time, the solution is exchanged as and when needed. After the tissue(s) is(are) submerged for appropriate time in Krebs' solution containing the compounds of the invention, the biogenic amine released during this period is quantified. The compound(s) of the invention, if appropriate, a positive control which is a known enhancer compound are dissolved in saline, as well as saline as a negative control, are subcutaneously administered 30 min before dissection of brain samples.

The amount of appropriate amine released for 20 min is measured, e.g. by chromatography, and is noted as nmol/g tissue. The differences among means are tested e.g. using Students t-test. Significance level is set e.g. at $P<0.05$.

It is expected that an enhancer compound increases monoamine neurotransmitter release. In particular a pure enhancer compound increases monoamine neurotransmitter release in a low concentration, e.g. in lower concentration than the effective concentration of a MAO inhibitor, in particular in a concentration less than 0.05 or 0.02 mg/kg per day or even more preferably not higher or lower than 0.015 mg/kg per day or 0.01 mg/kg per day or less than 0.005 or 0.002 mg/kg per day or even more preferably not higher or lower than 0.0015 mg/kg per day or 0.001 mg/kg per day.

INDUSTRIAL APPLICABILITY

The peculiar mechanism of action of the proper low specific enhancer doses of the enhancer substances forms the basis of their unique safety. In the extremely low dose in which they exert their specific enhancer effect, they selectively transform the lower performing enhancer sensitive neurons to better performing ones.

Since a bi-modal, bell-shaped concentration effect curve is characteristic to the enhancer effect, a given concentration range typical of the specific enhancer effect of the enhancer substance was needed for the appropriate performance, and both a lower and a higher concentration were less effective.

Lifelong preventive medication requires unique drug safeness. All drugs used today harshly change the physiological milieu of the highly sophisticated living material, so they are, in principle, incompatible for lifelong daily administration. In contrast, the synthetic enhancer substances of the present invention, in particular in the low concentration in which they exert their specific enhancer effect, transform the lower performing enhancer-sensitive neurons for better performing ones—leaving the physiological milieu of the neurons unchanged—are suitable for lifelong preventive medication.

The enhancer substances, e.g. Deprenyl or PPAP of the present invention exert their specific enhancer effect in a very low dose. As typically, as exemplified by Deprenyl, they are tolerated in a higher dose, the savety margin of these compounds are unique. The discovery of a previously unknown mechanism by the present inventors, a tumor-manifestation-suppressing (TMS) regulation in the mammalian brain, is an example for previously unknown enhancer-sensitive brain regulation.

The present inventors disclose herein the first time a tumor suppression mechanism based on the catecholaminergic specific enhancer activity of a syntetic phenylethylamine analog compounds. The present results show that enhancer substances of the present invention increase the activity of the catecholaminergic neurons qualitatively differently from any of the drugs used for this purpose today.

The invention relates to pharmaceutical preparations, in particular medicaments for use in the prevention and treatment of cancer, in particular suppression of tumor manifestation as well as methods for the same.

REFERENCES

Ahmed H, Shah N. (2000) Formulation of low dose medicines—theory and practice. Am. Pharm. Rev. 3(3): 9-14

Archer, J R & Harrison, D E (1996) L-Deprenyl treatment in aged mice slightly increases life spans, and greatly reduces fecundity by aged males. J Gerontol Ser A—Biol Sci Med, 51: B448-453.

Bickford, P C, Adams, S J, Boyson, P, et al. (1997) Long-term treatment of male F344 rats with deprenyl: assessment of effects on longevity, behavior, and brain function. Neurobiol Aging, 3:309-318.

Clarke A et al. (2003). A new low-dose formulation of selegiline: clinical efficacy, patient preference and selectivity for MAO-B inhibition. J Neural Transm. 110(11): 1257-71

Dalló, J & Köles, L (1996) Longevity treatment with (−)-deprenyl in female rats: effect on copulatory activity and lifespan. Acta Physiologica Hungarica 84:277-278.

Fowler, Joanna S. et al., (29 Oct. 2014) Evidence that Formulations of the Selective MAO-B Inhibitor, Selegiline, which Bypass First-Pass Metabolism, also Inhibit MAO-A in the Human Brain; Neuropsychopharmacology advance online publication. published on-line; doi: 10.1038/npp.2014.214

Freisleben, H J, Lehr, F, Fuchs, J (1994) Lifespan of immunosuppressed NMRI-mice is increased by (−)-deprenyl. J Neural Transm Suppl., 41: 231-236.

Jacobsen P F, Jenkyn D J, Papdimitriou J M (1985) Establishment of a human medulloblastoma cell line and its heterotransplantation into nude mice. J Neuropathol Exp Neurol 44:472-485.

Jordens, R G, Berry, M D, Gillott, C, et al. (1999) Prolongation of life in an experimental model of aging in Drosophila Melanogaster. Neurochem Res 24:227-233.

Keles G E, Berger M S, Srinivasan J et al (1995) Establishment and characterization of four human medulloblastoma cell lines. Oncol Res 7:493:503.

Kitani, K, Kanai, S, Sato, Y, et al. (1993) Chronic treatment of (−)deprenyl prolongs the life span of male Fischer 344 rats. Further evidence. Life Sci 52:281-288.

Kitani K, Kanai S, Ivy G O, Carrillo M C, (1998) "Assessing the effects of deprenyl on longevity and antioxidant defenses in different animal models" Annals of the New York Acadey of Sciences 854 291-306

Knoll J (1988) The striatal dopamine dependency of life span in male rats. Longevity study with (−)deprenyl. Mech Ageing Dev 46:237-262.

Knoll J (1994) Memories of my 45 years in research. Pharmacol Toxicol 75:65-72

Knoll J, Knoll B and Miklya I (1996) "High performing rats are more sensitive toward catecholaminergic activity enhancer (CAE) compounds than their low performing peers" Life Sci 58:945-952

Knoll J (1998) (−)Deprenyl (selegiline) a catecholaminergic activity enhancer (CAE) substance acting in the brain. Pharmacol Toxicol 82:57-66.

Knoll J (2001) Antiaging compounds: (−)Deprenyl (Selegiline) and (−)1-(benzofuran-2-yl)-2-propylaminopentane, (−)BPAP, a selective highly potent enhancer of the impulse propagation mediated release of catecholamines and serotonin in the brain. CNS Drug Rev 7:317-345

Knoll J (2003) Enhancer regulation/endogenous and synthetic enhancer compounds: A neurochemical concept of the innate and acquired drives. Neurochem Res 28:1187-1209

Knoll J (2005) The Brain and Its Self. A Neurochemical Concept if the Innate and Acquired Drives. Berlin, Heidelberg, New York: Springer; p. 1-176.

Knoll J (2006) Az agy és tudata. A velesztiletett és szerzett hajtóerök neurokémiai koncepciója. Akadémiai Kiadó, Budapest, 266 oldal.

Knoll J (2012) How Selegiline ((−)-Deprenyl) Slows Brain Aging. Bentham e-Books

Knoll J, Magyar K (1972) Some puzzling effects of monoamine oxidase inhibitors. Adv. Bioch Psychopharmacol 5:393-408

Knoll, J, Ecsery, Z, Kelemen, K, Nievel, J, Knoll, B (1964) Phenylisopropylmethyl-propinylamine HCL (E-250) egy új hatásspektrumú pszichoenergetikum. MTA V. Oszt. Közl. 15: 231-238.

Knoll, J, Ecseri, Z, Kelemen, K, Nievel, J, Knoll, B (1965) Phenylisopropylmethyl propinylamine (E-250) a new psychic energizer. Arch int Pharmacodyn Thér 155:154-164.

Knoll J, Vizi E S, Somogyi G (1968) Phenylisopropylmethylpropinylamine (E-250), a monoamine oxidase inhibitor antagonizing the effects of tyramine. Arzneimittelf 18:109-112

Knoll J, Dallo J, Yen T T (1989) Striatal dopamine, sexual activity and lifespan. Longevity of rats treated with (−)deprenyl. Life Sci 45:525-531.

Knoll J, Knoll B, Török Z, Timár J, Yasar S (1992) The pharmacology of 1-phenyl-2-propylaminopentane (PPAP), a deprenyl-derived new spectrum psychostimulant. Arch int Pharmacodyn Thér 316:5-29

Knoll J, Yen T T, Miklya I (1994) Sexually low performing male rats die earlier than their high performing peers and (−)deprenyl treatment eliminates this difference. Life Sciences 54:1047-1057.

Knoll, J & Miklya, I (1994), 'Multiple, small dose administration of (−)deprenyl enhances catecholaminergic activity and diminishes serotoninergic activity in the brain and these effects are unrelated to MAO-B inhibition', *Archives internationales de Pharmacodynamie et de Thérapie*, 328:1-15

Knoll J, Miklya I (1995) Enhanced catecholaminergic and serotoninergic activity in rat brain from weaning to sexual maturity:rationale for preventive (−)deprenyl medication. Life Sciences 56:611-620.

Knoll J, Yoneda F, Knoll B, Ohde H, Miklya I (1999) (−)1-(Benzofuran-2-yl)-2-propylaminopentane, [(−)BPAP], a selective enhancer of the impulse propagation mediated release of catecholamines and serotonin in the brain. Br J Pharmacol 128:1723-1732.

Knoll J, Miklya I, Knoll B, Dalló J (2000) Sexual hormones terminate in the rat the significantly enhanced catecholaminergic/serotoninergic tone in the brain characteristic to the post-weaning period. Life Sci 67:765-773

Knoll J, Miklya I, Knoll B (2002) Stimulation of the catecholaminergic and serotoninergic neurons in the rat brain by R-(−)-1-(benzofuran-2-yl)-2-propylaminopentane, (−)-BPAP. Life Sci 71:2137-2144

Lancet Editorial (1982) Deprenyl in Parkinson's Disease. The Lancet 2:695-696.

Miklya I (2011) The Knoll-concept to decrease the prevalence of Parkinson's disease. Chapter 5 In: David I. finkelstein (Ed.), Towards new therapies for Parkinson's Disease, InTech Open Acces Publisher (www.intechopen.com), pp. 77-100.

Miklya I, Knoll J (2003) Analysis of the effect of (−)-BPAP, a selective enhancer of the impulse propagation mediated release of catecholamines and serotonin in the brain. Life Sci 72:2915-2921

Milgram, M W, Racine, R J, Nellis, P, et al. (1990) Maintenance on L-(−)deprenyl prolongs life in aged male rats. Life Sci 47:415-420.

Ruehl, W W, Entriken, T L, Muggenberg, B A, et al. (1997) Treatment with L-deprenyl prolongs life in elderly dogs. Life Sci 61:1037-1044.

Stoll, S, Hafner, U, Kranzlin, B, Muller, W E (1997) Chronic treatment of Syrian hamsters with low-dose selegiline increases life span in females but not males. Neurobiol Aging 18:205-211.

Taketo, M., Schroeder, A. C., Mobraaten, L. E. et al., (1991) FVB/N: An inbred mouse strain preferable for transgenic analyses. Proc. Natl. Acad. Sci. USA 88:2065-2069

ThyagaRajan S, Felten S Y, Felten D L. (1998) Antitumor effect of L-deprenyl in rats with carcinogen-induced mammary tumors. 123(2) 177-83.

Waldmann, T A (March 2003). "Immunotherapy: past, present and future.". *Nature Medicine* 9 (3): 269-77

Weinberg, Robert A (2014). "The Biology of Cancer." Garland Science

Zheng Jack (2009) Formulation and Analytical Development for Low-Dose Oral Drug Products. John Wiley & Sons

The invention claimed is:

1. A method for treating or suppressing manifestation of a cancer or a metastasis thereof wherein the cancer is a carcinoma or a sarcoma, said method comprising administering to a mammal in need thereof a neuronal activity enhancer compound having formula IV or a pharmaceutically acceptable salt thereof, in a daily dose lower than 0.01 mg per kg body weight wherein this is a specific enhancer dose, which stimulates enhancer-sensitive neurons in the brain and having a specific enhancer effect thereon, wherein said compound is a cathecholaminergic enhancer compound which enhances impulse propagation mediated release of a cathecholamine neurotransmitter from catecholaminergic neurons in the central nervous system,

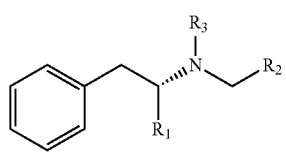

IV wherein
$R_1$ is methyl, ethyl or propyl;
$R_2$ is methyl, ethyl, ethynyl or propyl;
$R_3$ is hydrogen, methyl or ethyl.

2. The method of claim 1 wherein $R_2$ is $C_{2-3}$ alkyl, $C_{2-3}$ alkenyl or $C_{2-3}$ alkynyl, and $R_3$ is hydrogen or methyl.

3. The method of claim 1 wherein
$R_2$ is ethyl or ethynyl; and
$R_3$ is hydrogen or methyl.

4. The method of claim 1 wherein said compound is (R)-1-Phenyl-N-propylpentan-2-amin ((−)-PPAP).

5. The method of claim 1 wherein said compound is
(R)—N-methyl-N-(1-phenylpropan-2-yl)prop-2-yn-1-amine (Selegiline or (−)-Deprenyl).

6. The method of claim 1 wherein the daily dose is lower than 0.005 mg/kg body weight wherein this is a specific enhancer dose.

7. The method of claim 6 wherein the daily dose is lower than 0.0025 mg/kg body weight wherein this is a specific enhancer dose.

8. The method of claim 1 wherein the mammal is a sexually mature human subject.

9. The method of claim 1 wherein the cancer is a malignant tumor or the cancer is selected from the group consisting of a carcinoma or a sarcoma of the connective tissue.

10. The method of claim 9 wherein the malignant tumor is selected from the group consisting of fibromyxosarcoma, adenocarcinoma, colon carcinoma and liver metastasis.

11. The method of claim 1 wherein said compound is administered to the mammal for at least 1, 2, 3, 5, 6, 8 or 10 months or for at least 1, 2, 3, 4, 5 or 6 years.

12. The method of claim 1 wherein the compound is administered in an amount in which said compound enhances impulse propagation mediated catecholamine release in central nervous system.

13. The method of claim 1 wherein said compound is
(R)—N-methyl-N-(1-phenylpropan-2-yl)prop-2-yn-1-amine (Selegiline or (−)-Deprenyl)
wherein the mammal is a sexually mature human subject.

14. The method of claim 13 wherein said compound is administered to the subject for at least 1, 2, 3, 5, 6, 8 or 10 months or for at least 1, 2, 3, 4, 5 or 6 years.

15. The method of claim 1 wherein $R_2$ is ethyl or ethynyl.

16. The method of claim 1 wherein the optical purity of the compound is higher than 80%.

* * * * *